US011594403B1

(12) United States Patent
Steingrimsson et al.

(10) Patent No.: US 11,594,403 B1
(45) Date of Patent: Feb. 28, 2023

(54) PREDICTIVE TEST FOR PROGNOSIS OF MYELODYSPLASTIC SYNDROME PATIENTS USING MASS SPECTROMETRY OF BLOOD-BASED SAMPLE

(71) Applicant: Biodesix, Inc., Boulder, CO (US)

(72) Inventors: Arni Steingrimsson, Steamboat Springs, CO (US); Heinrich Röder, Steamboat Springs, CO (US); Joanna Röder, Steamboat Springs, CO (US)

(73) Assignee: BIODESIX INC., Boulder, CO (US)

( * ) Notice: Subject to any disclaimer, the term of this patent is extended or adjusted under 35 U.S.C. 154(b) by 802 days.

(21) Appl. No.: 15/899,866

(22) Filed: Feb. 20, 2018

Related U.S. Application Data

(62) Division of application No. 14/946,045, filed on Nov. 19, 2015, now abandoned.

(60) Provisional application No. 62/086,807, filed on Dec. 3, 2014.

(51) Int. Cl.
| | |
|---|---|
| *G01N 33/48* | (2006.01) |
| *G01N 33/50* | (2006.01) |
| *H01J 49/00* | (2006.01) |
| *H01J 49/16* | (2006.01) |
| *H01J 49/40* | (2006.01) |
| *G01N 33/49* | (2006.01) |

(52) U.S. Cl.
CPC ......... *H01J 49/0036* (2013.01); *G01N 33/49* (2013.01); *H01J 49/164* (2013.01); *H01J 49/40* (2013.01)

(58) Field of Classification Search
CPC ...... H01J 49/0036; H01J 49/164; H01J 49/40; G01N 33/49
See application file for complete search history.

(56) References Cited

U.S. PATENT DOCUMENTS

| | | | |
|---|---|---|---|
| 7,727,968 B2 * | 6/2010 | Feingold | A61K 31/704 514/45 |
| 7,736,905 B2 | 6/2010 | Roder | |

(Continued)

OTHER PUBLICATIONS

Garcia-Manero, "CME Information: Myelodysplastic syndromes: 2014 update on diagnosis, risk-stratification and management", Am. J. Hemat., 89(1):98-108 (2014).

(Continued)

*Primary Examiner* — Russell S Negin
(74) *Attorney, Agent, or Firm* — DLA Piper LLP US

(57) ABSTRACT

A method of predicting whether an MDS patient has a good or poor prognosis uses a general purpose computer configured as a classifier and mass-spectrometry data obtained from a blood-based sample. The classifier assigns a classification label of either Early or Late (or the equivalent) to the patient's sample. Patients classified as Early are predicted to have a poor prognosis or worse survival whereas those patients classified as Late are predicted to have a relatively better prognosis and longer survival time. The groupings demonstrated a large effect size between groups in Kaplan-Meier analysis of survival. Most importantly, while the classifications generated were correlated with other prognostic factors, such as IPSS score and genetic category, multivariate and subgroup analysis showed that they had significant independent prognostic power complementary to the existing prognostic factors.

11 Claims, 15 Drawing Sheets

(56) References Cited

U.S. PATENT DOCUMENTS

| | | | |
|---|---|---|---|
| 2005/0086017 A1* | 4/2005 | Wang | H01J 49/0009 702/85 |
| 2011/0208433 A1 | 8/2011 | Grigorieva | |
| 2013/0320203 A1 | 12/2013 | Roder | |
| 2013/0344111 A1 | 12/2013 | Roder | |
| 2015/0102216 A1 | 4/2015 | Roder | |

OTHER PUBLICATIONS

Choi et al., "MicroRNA-194-5p could serve as a diagnostic and prognostic biomarker in myelodysplastic syndromes", Leukemia Research 39:763-768 (2015).

Cremers et al., "Immunophenotyping for diagnosis and prognosis in MDS: Ready for general application?", Best Practice and Research Clinical Haematology, 28:14-21 (2015).

Kern et al., "Multiparameter Flow Cytometry Provides Independent Prognostic Information in Patients with Suspected Myelodysplastic Syndromes: A Study on 804 Patients", Cytometry Part B Clinical Cytometry, 88B:154-164 (2015).

Minetto et al., "Combined assessment of WT1 and BAALC gene expression at diagnosis may improve leukemia-free survival predication in patients with myelodysplastic syndromes", Leukemia Research 39:866-873 (2015).

Ades et al., "Myelodysplastic syndromes", Lancet, 383:2239-52 (2014).

Loeffler-Ragg et al., "Serum CD44 levels predict survival in patients with low-risk myelodysplastic syndromes", Critical Review in Oncology/Hematology, 78:150-161 (2011).

Zuo et al., "circulating microRNAs let-7a and miR-16 predict progression-free survival and overall survival in patients with myelodysplastic syndrome", Blood, 118(2):413-415 (2011).

Mills et al., "Microarray-based classifiers and prognosis models identify subgroups with distinct clinical outcomes and high risk of AML transformation of myelodysplastic syndrome", Blood, 114(5): 1063-72 (2009).

Bejar, "Prognostic models in myelodysplastic syndromes", American Society of Hematology, pp. 504-510 (2013).

Westers et al., "Aberrant immunophenotype of blasts in myelodysplastic syndromes is a clinically relevant biomarker in predicting response to growth factor treatment", Blood, 115:1779-1784 (2010).

* cited by examiner

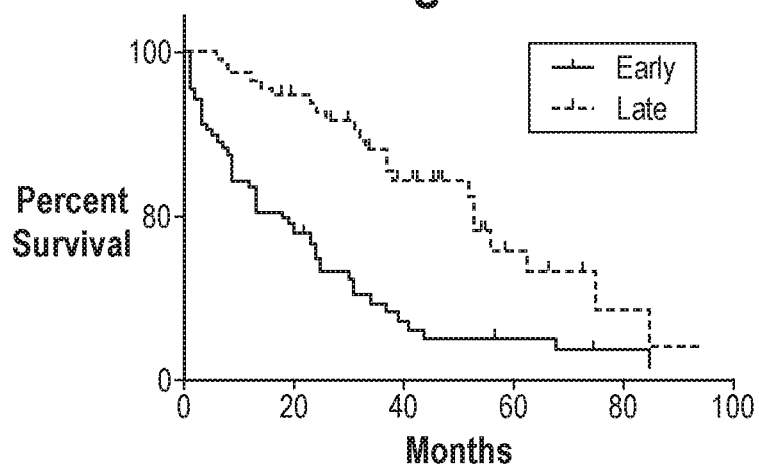
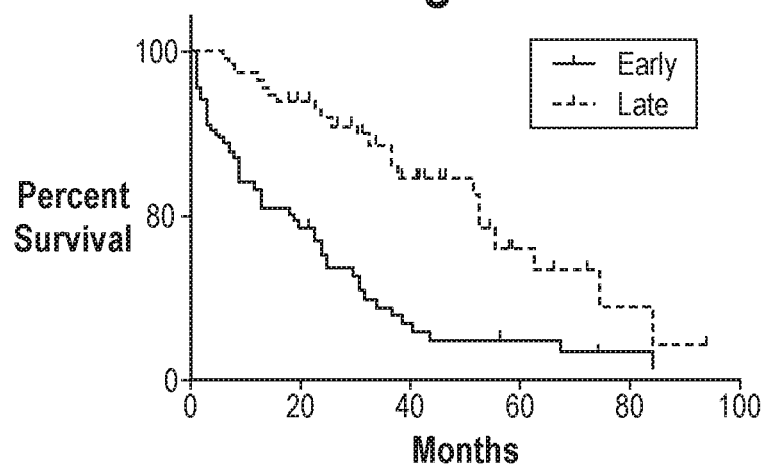

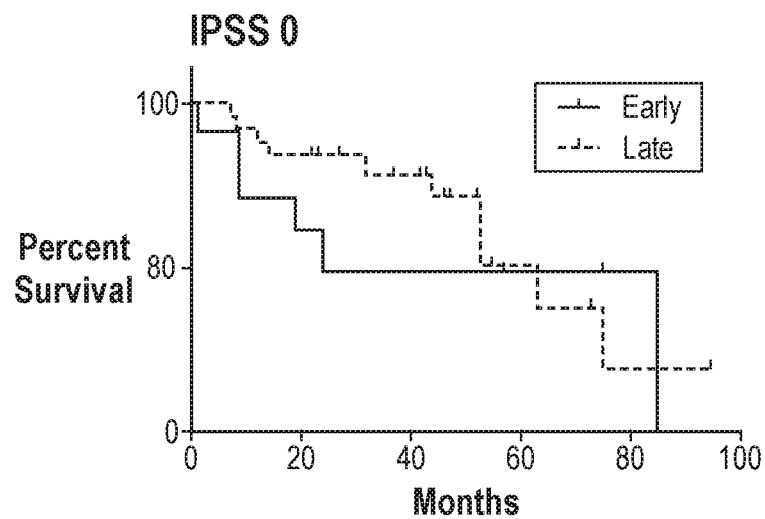
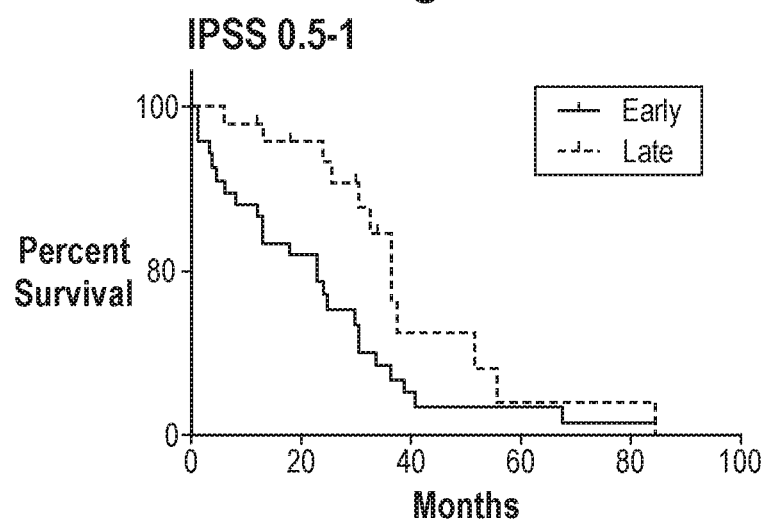

Good karyotype

HR = 0.39 (95% CI: 0.16-0.80)
log-rank p = 0.014

Gene: del5

HR = 0.30 (95% CI: 0.05-0.61)
log-rank p = 0.012

Gene: Intermediate

HR = 0.29 (95% CI: 0.06-0.94)
log-rank p = 0.050

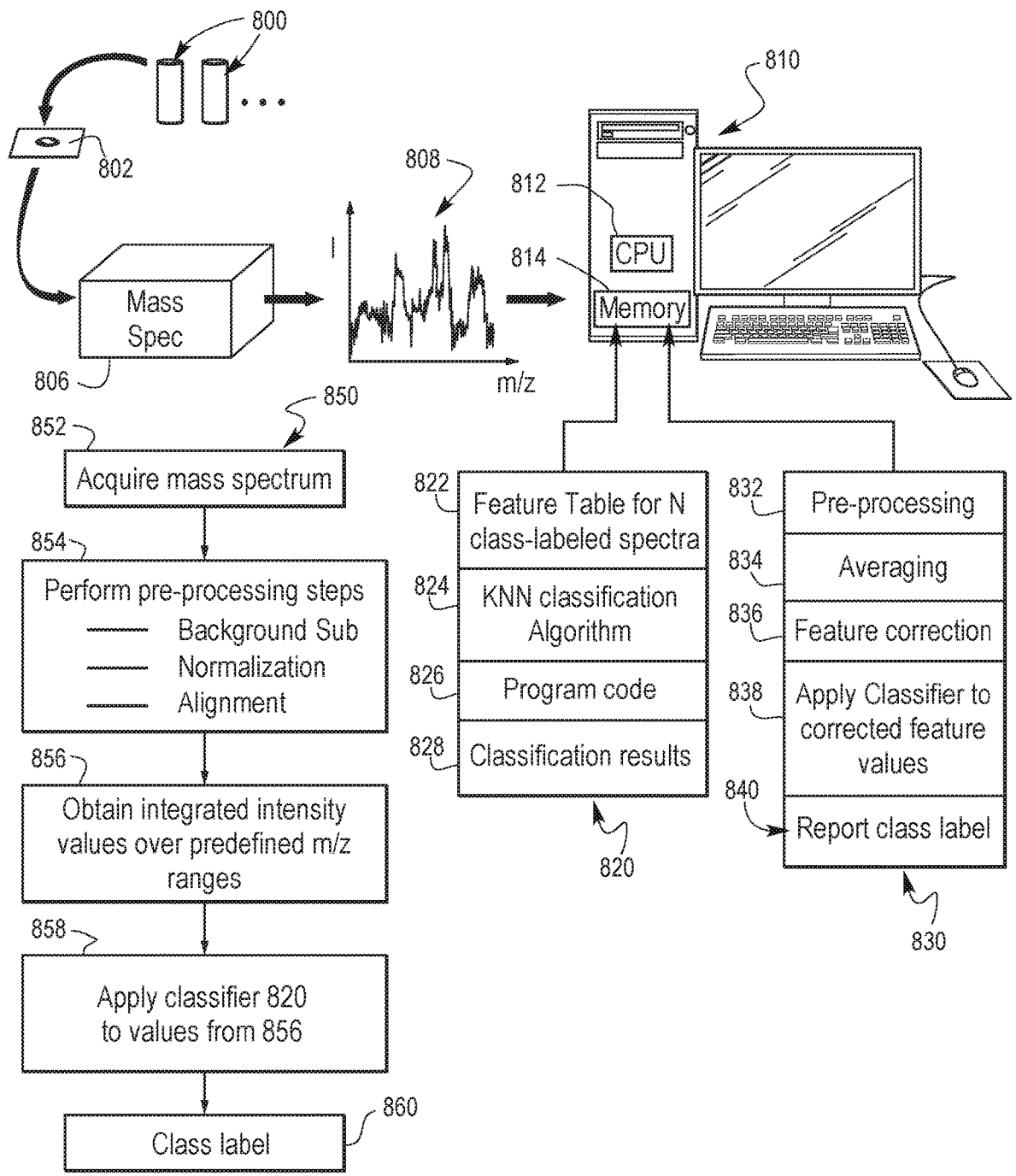

PREDICTIVE TEST FOR PROGNOSIS OF MYELODYSPLASTIC SYNDROME PATIENTS USING MASS SPECTROMETRY OF BLOOD-BASED SAMPLE

PRIORITY

This application is a divisional application of U.S. Ser. No. 14/946,045, filed on Nov. 19, 2015, which claims priority benefits under 35 U.S.C. § 119 to U.S. Provisional application Ser. No. 62/086,807 filed Dec. 3, 2014, all of which are incorporated by reference herein.

BACKGROUND

Myelodysplastic syndrome (MDS) comprises a heterogeneous group of myeloid hemopathies, characterized by ineffective bone marrow production of the myeloid class of blood cells. While the incidence of MDS in the general population is only about 4.5 per 100,000 people, the incidence of MDS rises steeply with age, such that the incidence rate exceeds 50 per 100,000 people over 80 years of age. MDS can arise de novo or occur after chemotherapy or radiation for prior malignancies. The major clinical problems facing patients with MDS are morbidities due to cytopenias (low blood counts) and the progression of MDS into acute myeloid leukemia (AML). National Comprehensive Cancer Network (NCCN) Guidelines, Version 1 Myelodysplastic Syndromes (2015).

MDS can be subdivided into several categories. Until recently, the French-American-British (FAB) categorization was used. This schema divided the syndrome into the five categories outlined in table 1. This categorization has now been superseded by the World Health Organization (WHO) classification, also described in Table 1.

TABLE 1

French-American-British and WHO categories of MDS

| FAB | WHO | Description |
| --- | --- | --- |
| Refractory anemia (RA) | Refractory anemia (RA) | Blasts < 5% in bone marrow, median survival from 2-5 years, progression to AML rare, 20%-30% of MDS patients. |
| | Refractory cytopenia with multilineage or unilineage dysplasia. | Blasts < 5% in bone marrow, multiple or single cytopenia present, median survival 33 months, 11% progression to AML, 15% of MDS patients. |
| Refractory anemia with ring sideroblasts (RARS) | Refractory anemia with ring sideroblasts (RARS) | Ring sideroblasts > 15% of marrow red cell precursors, 1%-2% progress to AML, prognosis as for RA, 10%-12% of MDS patients. |
| Refractory anemia with excess blasts (RAEB) | Refractory anemia with excess blasts −1 and −2 | RAEB-1: 5%-9% blasts in bone marrow and < 5% blasts in blood, median survival 18 months, 25% of patients progress to AML. RAEB-2: 10%-19% blasts in bone marrow, median survival 10 months, 33% of patients progress to AML. RAEB-1+RAEB-2 accounts for 40% of MDS patients. |
| | MDS, unclassifiable | |
| | MDS associated with del(5q) | Blasts in blood < 5%, associated with isolated del(5q) cytogenetic abnormality. Long survival, |

TABLE 1-continued

French-American-British and WHO categories of MDS

| FAB | WHO | Description |
| --- | --- | --- |
| Refractory anemia with excess blasts in transformation (RAEB-t) | Reclassified from MDS to AML following MDS | Multiple cytopenias, 5%-19% blasts in blood, 20%-30% blasts in bone marrow. |
| Chronic myelomonocytic leukemia (CMML) | Reclassified from MDS to myelodysplastic and myeloprofilerative diseases | <20% blasts in bone marrow and > $10^9$ monocytes/L in blood |

Sources: NCCN MDS Guidelines, available from the cancer.gov website, see link in our prior provisional application, specification.

Several prognostic scoring systems have been developed to help to stratify MDS for appropriate treatment regimens. These include the International Prognostic Scoring System (IPSS), the revised IPSS (IPSS-R), and the WHO-based Prognostic Scoring System (WPSS). The original IPSS score ranges from 0 (low risk) to over 2.5 (high risk) and is based on the percentage of blasts in marrow, the karyotype and presence and multiplicity of cytopenias. This scoring system proved inadequate for accurate patient stratification, resulting in the development of the IPSS-R (ranging from 0 (very good prognosis) to over 4 (very poor prognosis)), which uses a combination of cytogenetic status, percentage of marrow blasts, hemoglobin level, platelet level, and ANC level, and the WPSS (ranging from 0 (very low risk) to 6 (very high risk)), which combines WHO MDS category, karyotype, and presence of severe anemia.

In addition to these commonly used prognostic scores, there have been some investigations into blood-based biomarkers that might be able to improve patient stratification. One particular study, using the same samples that were made available to us for this project, studied serum CD44 (sCD44) and showed that it had potential to add information to the existing IPSS scoring system. Loeffler-Ragg J. et al., *Serum CD44 levels predict survival in patients with low-risk myelodysplastic syndromes* Crit. Rev. Oncol. Hematol. vol. 78 no. 2 pp. 150-61 (2011) In addition, attempts have been made to refine risk stratification or identify patients most likely to develop secondary acute myelogenous leukemia using circulating microRNAs (see Zuo Z., et al., *Circulating microRNAs let-7a and miR-16 predict progression free survival and overall survival in patients with myelodysplastic syndrome*, Blood vol. 118 no. 2 pp. 413-5 (2011)) or gene expression profile by microarrays (see Mills K. I., et al., *Microarray-based classifiers and prognosis models identify subgroups with distinct clinical outcomes and high risk of AML transformation of myelodysplastic syndrome* Blood vol. 114 no. 5 pp. 1063-72 (2009)). These potential biomarkers remain to be validated in independent datasets.

Other prior art of interest includes Garcia-Manero, G., *Myelodysplastic syndromes: 2014 update on diagnosis, risk stratification, and management*, Am. J. Hemat., Vol. 89. No. 1, pp. 98-18 Jan. 2014); Bejar, R., *Prognostic models in myelodisplatic syndromes*, Am. Soc. Of Hematology, p. 504-510 (2013); Ades, L. et al., *Myelodysplastic Syndromes*, The Lancet, vol. 383 pp. 2239-52 (Jun. 26, 2014); and Westers, T. M., et al., *Aberrant immunophenotype of blasts in myelodysplastic syndromes is a clinically relevant biomarker in predicting response to growth factor treatment* Blood vol. 115 pp. 1779-1784 (2010).

Treatment for MDS patients is determined by risk category. High and some intermediate risk patients, if considered candidates for intensive therapy, will receive hematopoietic stem cell transplants (HSCTs) or high intensity chemotherapy. Patients in this risk group unsuitable for intensive therapy receive azacitidine or decitabine and/or supportive care. Treatment for these high-risk, very poor prognosis patients is relatively well determined and there is little unmet need for additional tests in this patient subgroup. On the other hand, treatment alternatives for low risk and other intermediate risk patients are more varied, including lenalidomide, immunosuppressive therapy, or possibly azacitidine or supportive therapy, and here better tools for patient stratification would be beneficial. In particular it would be clinically useful to improve on the prognostic scoring systems to determine which patients might have significantly worse than average prognosis, as such systems can guide treatment of MDS patients. This invention meets that need.

SUMMARY

In a first aspect, a method for predicting prognosis of a myelodysplastic syndrome (MDS) patient is disclosed. The method includes a step of performing MALDI-TOF mass spectrometry on a blood-based sample obtained from the MDS patient by subjecting the sample to at least 100,000 laser shots and acquiring mass spectral data. This step can preferably make use of the so-called "deep MALDI" mass spectrometry technique described in U.S. Patent application of H. Röder et al., Ser. No. 13/836,436 filed Mar. 15, 2013, U.S. patent application publication no. 2013/0320203, assigned to the assignee of this invention, the contents of which are incorporated by reference herein, including automatic raster scanning of a spot on a MALDI plate and summation of spectra from multiple spots. The method includes a step of obtaining integrated intensity values in the mass spectral data of a multitude of pre-determined mass-spectral features, such as 50, 100, or all of the features listed in Appendix A. The method further includes the step of operating on the mass spectral data with a programmed computer implementing a classifier. The operating step compares the integrated intensity values with feature values of a reference set of class-labeled mass spectral data obtained from a multitude of MDS patients with a classification algorithm and generates a class label for the sample, wherein the class label is associated with a prognosis of the MDS patient.

In a preferred embodiment, the classifier is configured as a combination of filtered mini-classifiers using a regularized combination method using the techniques described below and in the pending U.S. patent application of H. Röder et al., Ser. No. 14/486,442 filed Sep. 15, 2014, U.S. patent application publication no. 2015/0102216 assigned to the assignee of this invention, the content of which is incorporated by reference herein.

In one embodiment, the obtaining step obtains integrated intensity values of at least 50 features listed in Appendix A, at least 100 features listed in Appendix A, or alternatively at least 300 features listed in Appendix A, such as all 318 features.

The classifier assigns a classification label of either Early or Late (or the equivalent) to the patient's sample. Patients classified as Early are predicted to have a poor prognosis or worse survival whereas those patients classified as Late are predicted to have a relatively better prognosis and longer survival time. The groupings demonstrated a large effect size between groups in Kaplan-Meier analysis of survival. Most importantly, while the classifications generated were correlated with other (known) prognostic factors, such as IPSS score and genetic category, multivariate and subgroup analysis showed that they had significant independent prognostic power complementary to the existing prognostic factors.

In another aspect, a classifier is disclosed for predicting the prognosis of a MDS patient. The classifier includes a memory storing a reference set of mass spectral data obtained from blood-based samples of a multitude of MDS patients, such as feature values of the features listed in Appendix A or some subset of such features, such as 50 or 100 of such features. The classifier also includes a programmed computer coded with instructions for implementing a classifier configured as a combination of filtered mini-classifiers with drop-out regularization.

In another aspect, a laboratory testing system for conducting tests on blood-based samples from MDS patients and predicting the prognosis of the MDS patients is disclosed. The laboratory testing system includes a MALDI-TOF mass spectrometer configured to conduct mass spectrometry on a blood-based sample from a patient by subjecting the sample to at least 100,000 laser shots and acquire resulting mass spectral data, a memory storing a reference set of mass spectral data obtained from blood-based samples of a multitude of MDS patients and associated class labels; and a programmed computer coded with instructions to implement a classifier configured as a combination of filtered mini-classifiers with drop-out regularization. The reference set of mass spectral data includes feature values of at least some of the m/z features listed in Appendix A. The programmed computer is programmed to generate a class label for the sample associated with the prognosis of the MDS patient, such as Early or Late.

BRIEF DESCRIPTION OF THE DRAWINGS

FIGS. 3A-3F are Kaplan-Meier plots for survival for patients with MDS (and having either RA, RAEB, RARS, or CMML, see Table 1 for the definitions) according to classifier label, Early or Late. The results are shown at each stage of the class label refinement process (i.e., successive iterations of loop 142 of FIG. 1) from FIG. 3A through FIG. 3F. The final classifier selected at step 144 of FIG. 1 as a majority vote of the master classifiers is shown in the last panel FIG. 3F.

FIGS. 5A-5I are Kaplan-Meier plots for survival of various prognostic sub-groups by Early and Late classifications, with FIG. 5A showing the plot for the patients with IPSS score of 0, FIG. 5B showing the plot for the patients with IPSS score of 0.5-1, FIG. 5C showing the plot for the patients with IPSS score of between 0 and 1; FIG. 5D showing the plot for the patients with IPSS score>1; FIG. 5E showing the plot for "Good karyotype" patients; FIG. 5F showing the plot for "Gene: del5" patients; FIG. 5G showing the plot for "Gene:Intermediate" patients; FIG. 5H showing the plot for biomarker "sCD44 low" patients, and FIG. 5I showing the plot for biomarker "sCD44 high" patients.

FIG. 8 is a schematic illustration of a laboratory testing system including mass spectrometer and programmed computer configured to classify a blood-based sample of an MDS patient to predict the prognosis of the patient.

DETAILED DESCRIPTION

Figure 1:
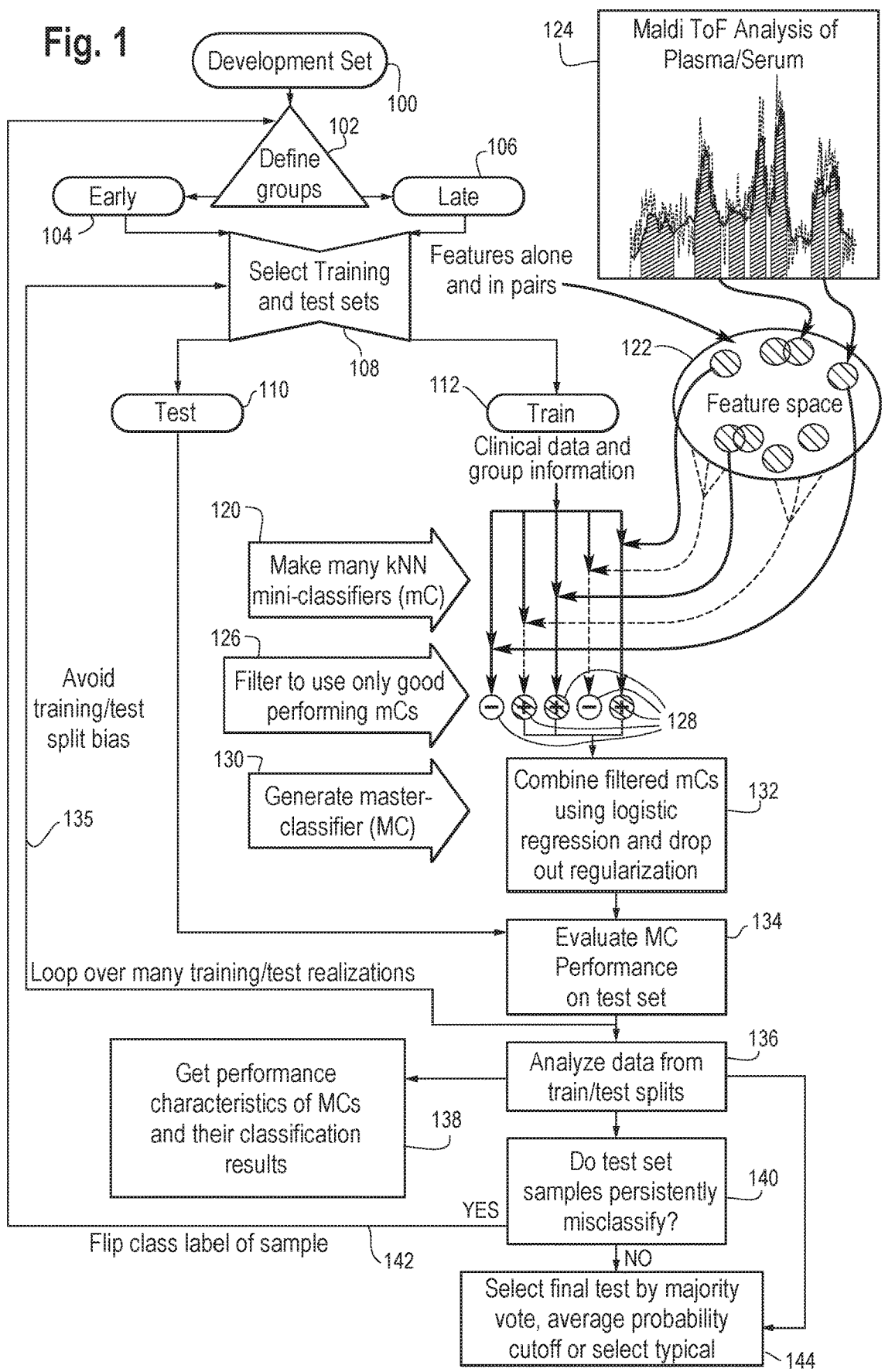
FIG. 1 is a flow-chart showing a classifier development methodology we used to create the classifiers disclosed in this document. The methodology uses mass-spectral data associated with blood-based samples obtained from patients with MDS.
Figure 2A:
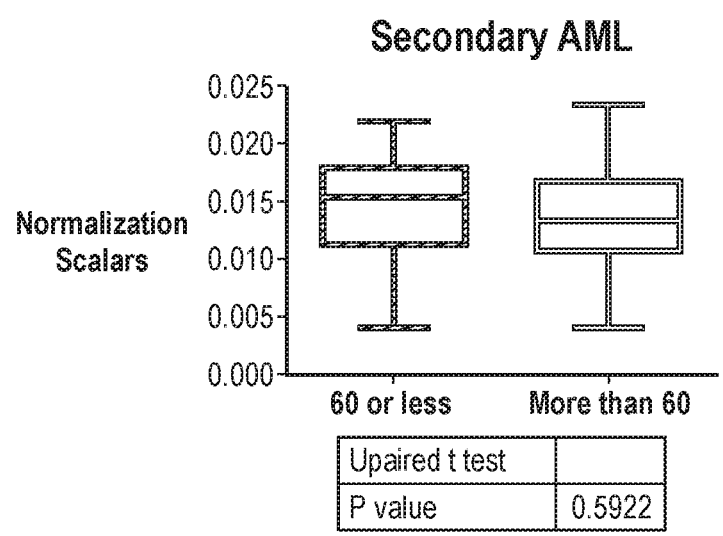
FIGS. 2A-2D are box and whisker plots showing the results of a normalization step in the preprocessing of mass spectral data to construct the classifiers of this disclosure.
Figure 2B:
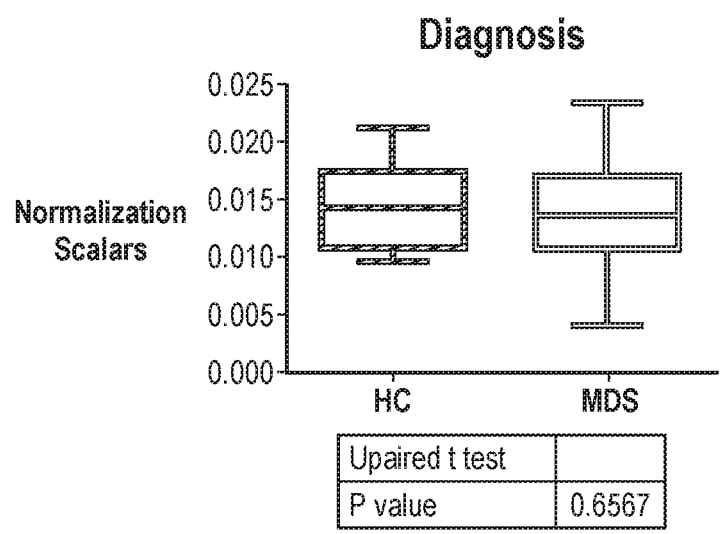
Figure 2C:
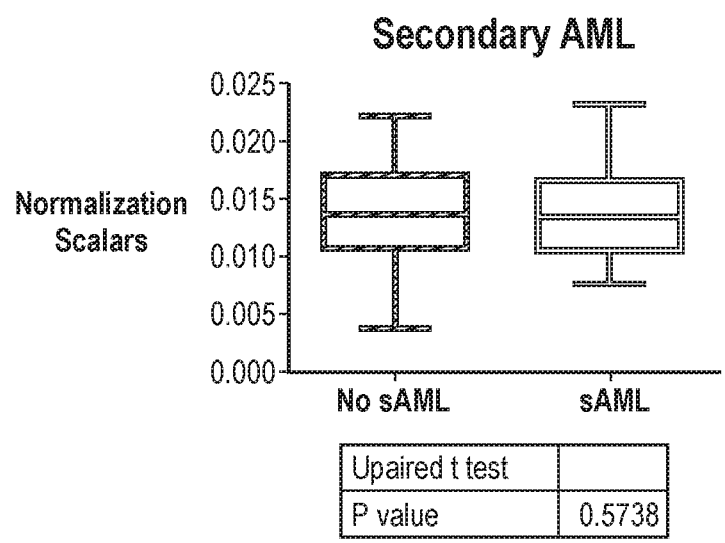
Figure 2D:
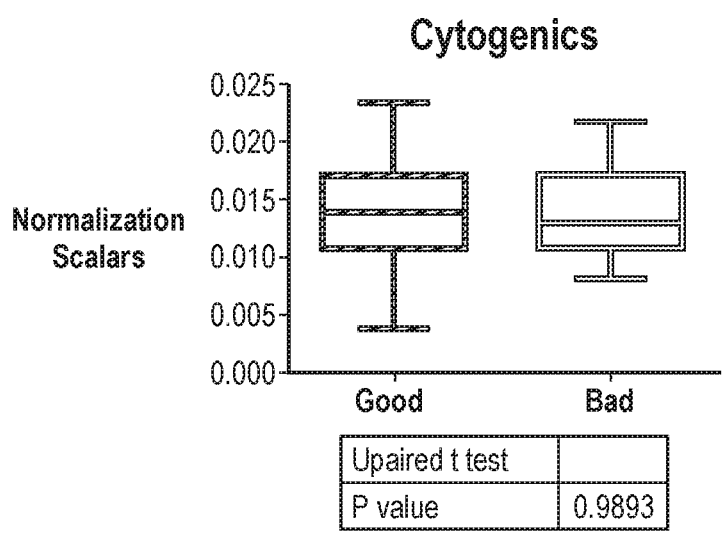

A method for assessing the prognosis of an MDS patient is disclosed, and in particular a method of determining whether an MDS patient is likely to have a relatively worse prognosis or conversely a relatively good prognosis. The method makes use of mass spectrometry data obtained from a blood-based sample obtained from the patient. The method also makes use of a computer configured as a classifier which operates to classify the mass spectrometry data with the aid of a reference set of class-labeled mass spectrometry data obtained from a plurality of blood-based samples from other MDS patients.

The methodology we describe in this document makes use of a MALDI-TOF mass spectrometry method in which the blood-based sample is subject to at least 100,000 laser shots. This methodology allows greater spectral information to be obtained from the sample than normally acquired using standard "dilute and shoot" MALDI-TOF methods, which typically use only ~1000 to 2000 shots. The methodology preferably make uses of the so-called "deep MALDI" mass spectrometry technique described in U.S. Patent application of H. Röder et al., Ser. No. 13/836,436 filed Mar. 15, 2013, U.S. patent application publication no. 2013/0320203 assigned to the assignee of this invention, the contents of which are incorporated by reference herein. This methodology will be described in some detail in the following detailed description and the discussion of FIG. 8 later in this document.

The method continues with a step of operating on the mass spectral data with a programmed computer implementing a classifier. In a preferred embodiment, the classifier is implemented as a combination of filtered mini-classifiers using a regularized combination method. The classifier is referred to herein as a "CMC/D" classifier (Combination of Mini-Classifiers with Dropout regularization), and makes use of the classifier generation method described in pending U.S. patent application of H. Röder et al., Ser. No. 14/486,442 filed Sep. 15, 2014, U.S. patent application publication no. 2015/0102216 assigned to the assignee of this invention, the content of which is incorporated by reference herein. This method of generating the classifier from a development set of sample data (mass spectrometry data) will be discussed below in conjunction with FIG. 1. The method of using the classifier to generate a class label to predict the prognosis of the MDS patient is described in detail below in conjunction with FIG. 8.

In the operating step, the classifier compares the integrated intensity values with feature values of a reference set of class-labeled mass spectral data obtained from a multitude of MDS patients and generates a class label for the sample. This step may make use of a classification algorithm such as k-nearest neighbor (KNN) and select a class label by majority vote of the nearest neighbors in a multidimensional feature space. The class label, e.g., Early or the equivalent or Late or the equivalent, is predictive of the patient's prognosis, namely if the patient's mass spectrum is classified with an Early class label the patient is predicted to have a relatively poor prognosis, whereas if the patient's mass spectrum is classified with a Late class label the patient is predicted to have a good prognosis. The reference set of class-labeled mass spectral data may take the form of a training set used to develop the classifier, or may take the form of some subset of the training set.

It is envisioned that it would be possible to perform a classification test for a specific subtype of MDS, such as a RA classifier described below for the RA subtype of MDS.

We also describe the mass spectrometry features (m/z ranges) which are used for classification. The use of deep MALDI mass spectrometry reveals hundreds of potential features for classification (i.e., features at which integrated intensity values are obtained from the spectrum under test and features for which integrated intensity values are stored from the reference set). In one embodiment, the integrated intensity values are obtained from at least 50 features listed in Appendix A, such as 50 features, 100 features, 300 features, or all 318 of the features.

Our work in discovering the classifier and methodology of predicting the prognosis of an MDS patient occurred as a result of conducting mass spectrometry on a set of blood-based samples from MDS patients. This study, the samples we used, and the method of generating deep MALDI spectra will be described first. Then we will describe certain processing steps performed on the spectra post-acquisition to arrive at a development sample set. We will then describe our methodology of creating the classifier, including performance characteristics of a variety of classifiers we created. Later, this document will describe a representative practical testing environment in which the invention can be practiced, for example in a laboratory setting as a fee-for-service.

I. The Study, Spectral Acquisition, Post-Processing and Classifier Development

Available Samples and Clinical Data

One hundred and forty nine serum samples were available for classifier development, from patients with myelodysplastic syndrome (MDS), acute myelogenous leukemia (AML), and healthy controls. The patients were enrolled in the study described in Loeffler-Ragg J., et al., *Serum CD44 levels predict survival in patients with low-risk myelodysplastic syndromes* Crit. Rev. Oncol. Hematol. vol. 78 no. 2 pp. 150-61 (2011). One sample (sample ID 111) was hemolyzed and so could not be used. Patients were divided into seven groups according to FAB categorization: six patients presenting with AML, 17 patients with chronic myelomonocytic leukemia (CMML), 46 patients with refractory anemia (RA), 29 patients with refractory anemia with excess blasts (RAEB), 17 patients with refractory anemia with excess blasts in transformation (RAEB-t), 14 patients with refractory anemia with ring sideroblasts (RARS), and 19 healthy controls. This categorization follows the now outdated French-American-British (FAB) classification scheme. Under the current WHO categories, patients in the RAEB-t category are now also considered as having AML. For the purposes of this investigation, the healthy patients and those classified by WHO as having AML were not considered.

Some of the clinical characteristics are summarized by patient group in table 2.

minutes. Twenty microliters of the filtrate from each sample was then transferred to a 0.5 ml eppendorf tube for MALDI analysis.

All subsequent sample preparation steps were carried out in a custom designed humidity and temperature control chamber (Coy Laboratory). The temperature was set to 30° C. and the relative humidity at 10%.

TABLE 2

| Baseline clinical and laboratory data for the patients within each clinical group | | | | | | | |
|---|---|---|---|---|---|---|---|
| | AML n = 6 | CMML n = 17 | RA n = 46 | RAEB n = 29 | RAEB-t n = 17 | RARS n = 14 | Controls n = 19 |
| Age | | | | | | | |
| median (range) | 76 (58-89) | 73 (44-86) | 66.5 (23-93) | 69 (19-85) | 63 (52-82) | 68.5 (51-84) | 51 (20-93) |
| Gender | | | | | | | |
| male | 2 | 9 | 25 | 18 | 13 | 7 | 9 |
| female | 4 | 8 | 21 | 11 | 3 | 7 | 10 |
| Blasts | | | | | | | |
| median (range) | 61 (32-89) | 4 (1-13) | 2 (0-5.5) | 9 (5-19) | 23 (6-20) | 1 (0-4.5) | — |
| Genetic marker | | | | | | | |
| good karyotype | 3 | 12 | 17 | 12 | 6 | 8 | 0 |
| del5 | 0 | 0 | 11 | 6 | 0 | 1 | 0 |
| intermediate | 0 | 2 | 4 | 4 | 3 | 3 | 0 |
| bad karyotype | 1 | 2 | 3 | 3 | 7 | 0 | 0 |
| IPSS | | | | | | | |
| 0 | 0 | 4 | 24 | 0 | 0 | 8 | 0 |
| 0.5 | 0 | 4 | 9 | 6 | 1 | 4 | 0 |
| 1.0 | 0 | 5 | 6 | 12 | 0 | 1 | 0 |
| 1.5 | 0 | 1 | 2 | 1 | 0 | 0 | 0 |
| 2.0 | 1 | 2 | 0 | 4 | 2 | 0 | 0 |
| 2.5 | 4 | 0 | 0 | 2 | 3 | 0 | 0 |
| sCD44 | | | | | | | |
| median (range) | 872 (459-1757) | 1020 (570-7961) | 586 (340-1210) | 595 (301-1077) | 774 (350-1138) | 547 (360-911) | 487 (325-890) |
| sEcad | | | | | | | |
| median (range) | 99 (63-128) | 87 (36-230) | 68 (0.2-286) | 104 (32-221) | 73 (40-146) | 83 (57-131) | 83 (57-188) |
| Secondary AML | | | | | | | |
| No | 0 | 14 | 34 | 11 | 4 | 12 | 0 |
| Yes | 6 | 2 | 6 | 10 | 9 | 1 | 0 |
| Unknown | 0 | 1 | 6 | 8 | 4 | 1 | 19 |

NA = not available

Spectral Acquisition

A. Sample Preparation

Samples were thawed and 3 µl aliquots of each experimental sample and quality control reference serum (a pooled sample obtained from serum from five healthy patients purchased from ProMedDx) spotted onto VeriStrat© cellulose serum cards (Therapak). The cards were allowed to dry for 1 hour at ambient temperature after which the whole serum spot was punched out with a 6 mm skin biopsy punch (Acuderm). Each punch was placed in a centrifugal filter with 0.45 µm nylon membrane (VWR). One hundred µl of HPLC grade water (JT Baker) was added to the centrifugal filter containing the punch. The punches were vortexed gently for 10 minutes then spun down at 14,000 rcf for 2 minutes. The flow-through was removed and transferred back on to the punch for a second round of extraction. For the second round of extraction, the punches were vortexed gently for 3 minutes then spun down at 14,000 rcf for 2

An equal volume of freshly prepared matrix (25 mg of sinapinic acid dissolved in 1 ml of 50% acetonitrile: 50% water plus 0.1% TFA) was added to each 20 µl serum extract and the mix vortexed for 30 sec. The first three aliquots (2×2 µl) of sample:matrix mix were discarded into the tube cap. Three aliquots of 2 µl sample:matrix mix were then spotted onto a polished steel MALDI target plate (Bruker Daltonics). The MALDI target was allowed to dry in the chamber before placement in the MALDI mass spectrometer.

This set of samples (148 experimental samples plus QC sample) was processed for MALDI analysis in three batches. Batches one, two, and three contained 50, 49, and 49 experimental samples plus 6 reference sample preparations, respectively. The preparations of the reference sample were added to the beginning (2 preparations), middle (2 preparations), and end (2 preparations) of each of these three batches.

B. Acquisition of Mass Spectra

MALDI spectra were obtained using a MALDI-TOF mass spectrometer (Ultraflextreme from Bruker Daltonics, Bremen, Germany) equipped with a 2000 Hz SmartBeam laser. Data were acquired with positive ion detection in linear mode with the following settings: accelerating voltage set to 25 kV, extraction voltage set to 23.15 kV, lens voltage set to 7 kV, and the delayed extraction time set to 200 ns. The instrument was externally calibrated using the Bruker Protein Standard Mix consisting of insulin, ubiquitin, cytochrome c, and myoglobin.

Eight hundred shot spectra were collected from 63 pre-defined positions per MALDI spot (63×800×3 spots per sample) for a total of 151,200 laser shots per sample. While in this example spectra from a total of 151,200 laser shots were done so that 189 (63×3) 800-shot spectra were acquired, we believe that suitable deep spectral information would be obtained as long as good quality spectra from at least 100,000 laser shots can be averaged. It would be possible to obtain spectra averaged from an even greater number of shots, such as 500,000 or 1,000,000 shots, using the techniques of the deep-MALDI patent application cited previously. During spectral acquisition fuzzy control for laser power was turned off. No evaluation criteria were used during acquisition to filter out spectra. All filtering and processing of spectra was done post-acquisition.

Spectral Post-Processing

A. Averaging of Spectra to Produce One Spectrum Per Sample

There were 189 (63×3) replicate 800-shot spectra available for each patient acquired using deep MALDI instrument settings. The spectra were filtered using a ripple filter to remove artificial noise resulting from the digital converter. The background was subtracted for the purpose of finding peaks to be used in alignment. The threshold for peak detection was set to a signal to noise ratio of 3. The raw spectra (no background subtraction) were then aligned using the calibration points listed in table 3. Only spectra with a minimum of 20 peaks detected and having used 5 alignment points were considered for inclusion in the average. An average for each sample was created by selecting 112 aligned replicate spectra at random resulting in an average spectrum of about 90K shots.

TABLE 3

Calibration points used to align the raw spectra prior to averaging

| | m/z |
|---|---|
| 1 | 4153 |
| 2 | 4183 |
| 3 | 6433 |
| 4 | 6631 |
| 5 | 8206 |
| 6 | 8684 |
| 7 | 9133 |
| 8 | 11527 |
| 9 | 12572 |
| 10 | 23864 |
| 11 | 13763 |
| 12 | 13882 |
| 13 | 14040 |
| 14 | 15127 |
| 15 | 15869 |
| 16 | 17253 |
| 17 | 18630 |
| 18 | 21066 |
| 19 | 28108 |
| 20 | 28316 |

B. Preprocessing of Averaged Spectra

The spectra were background subtracted (two windows 80,000/10,000) and normalized using the partial ion current (PIC) windows listed in the table below (table 4). Background subtraction of mass spectrometry is known in the art and described in the prior patent of Biodesix, Inc., U.S. Pat. No. 7,736,905, the content of which is incorporated by reference herein. Partial ion current normalization is also explained in the '905 patent.

TABLE 4

Normalization windows used in pre-processing the spectra, left and right m/z boundaries

| Left M/Z | Right M/Z |
|---|---|
| 3748 | 3787 |
| 5918 | 6038 |
| 6164 | 6244 |
| 7339 | 7518 |
| 10542 | 10592 |
| 12246 | 12352 |
| 18385 | 18521 |
| 22077 | 22883 |
| 22889 | 23893 |

These windows were selected with a method that protects against using windows that are significantly different between groups of interest (e.g., Healthy control vs MDS), which could lead to a reduction in classification potential, and also against features that are intrinsically unstable. The entire m/z region was divided into 92 bins that varied in size to prevent the bin boundaries from landing within peaks. For each m/z bin, feature values were determined for each sample. The feature values were compared using a Wilcoxon rank-sum test by the group comparisons listed in table 5. If the resulting p value was between 0-0.1, the region was excluded from normalization. If the CV of the feature values (all samples) was greater than 1.0, the region was excluded. The 9 windows above met the requirement for all 4 group comparisons.

TABLE 5

Group comparisons used to test normalization window dependency on clinical group

| Group | Comparison |
|---|---|
| 1 | Age 60 or less versus more than 60 |
| 2 | Healthy Control versus MDS |
| 3 | No Secondary AML versus Secondary AML |
| 4 | Cytogenetics good versus bad |

Using these 9 bins as PIC normalization windows a normalization scalar was calculated for each sample. A final comparison of groups was performed using the normalization scalars to ensure that the groups and the normalization parameters used were not significantly correlated. The box and whisker plots of FIG. 2 demonstrate that the groups have similar distributions of normalization scalars.

The spectra were then calibrated using the calibration points listed in table 6 to remove slight differences in alignment.

TABLE 6

Calibration points used to align the Deep MALDI average spectra

| | M/Z |
|---|---|
| 1 | 4153 |
| 2 | 4185 |
| 3 | 6433 |
| 4 | 6631 |
| 5 | 6940 |
| 6 | 7563 |
| 7 | 7934 |
| 8 | 8915 |
| 9 | 9420 |
| 10 | 12862 |
| 11 | 13761 |
| 12 | 13879 |
| 13 | 14040 |
| 14 | 15128 |
| 15 | 15869 |
| 16 | 17255 |
| 17 | 17383 |
| 18 | 28108 |
| 19 | 28316 |

C. Feature Definitions

Feature definitions (m/z ranges) for use in classification were selected by viewing a subset of spectra from patients with "early" death (<12 months) compared to a "late" group with long survival (>36 months). Only patients with CMML, RA, RAEB, or RARS were included. Left and right peak boundaries were assigned by assessing the compilation of spectra for each feature. This process ensures the features are adequately captured for any individual spectrum. Feature definitions were allowed to overlap for neighboring features. A total of 318 features were identified and can be found in Appendix A. The feature definitions were applied to each spectrum in the development sample set to create a feature table of feature values (integrated intensity values for each feature).

D. Analysis of Reference Samples by Batch

Six preparations of reference sample (quality control sample) were prepared along with the experimental samples in each batch. Two of these preparations were plated at the beginning (rep 1 and 2), two at the end (rep 5 and 6), and 2 preparations were plated amid the experimental samples (rep 3 and 4). The purpose of the reference samples was to provide a common sample in each batch that could be used to correct the batches for expected day to day fluctuations in spectral acquisition. The reference samples were preprocessed as described above.

A set of feature definitions, specific to the reference sample and selected for their stability, was applied to the spectra. These feature definitions can be found in Appendix B of our prior provisional application, incorporated by reference. The resulting feature table was used only in the analysis of the reference samples. The reference sample spectra were analyzed to find two replicates that were most similar from the beginning and end of each batch. We compared each possible combination of replicates (1 and 5, 1 and 6, 2 and 5, 2 and 6) using the function:

A=min(abs(1−ftrval1/ftrval2),abs(1−ftrval2/ftrval1))

where ftrval1 (ftrval2) is the value of a feature for the first (second) replicate of the replicate pair. This quantity A gives a measure of how similar the replicates of the pair are. The average of A was calculated across all possible combinations of beginning and end reference sample ("SerumP2") replicate pairs for all features. The resulting list was sorted by increasing values of A. The lowest 20 were used to determine the most similar combinations of reference sample replicates taken from the beginning and ends of the batches. This process prevents the use of an outlier replicate spectrum in the batch correction procedure. Table 7 lists the features that were used to determine the most similar replicate combinations.

TABLE 7

The 20 most stable features considering beginning and end of batch reference spectra replicates

| m/z |
|---|
| 3365 |
| 4014 |
| 4289 |
| 4712 |
| 4783 |
| 5106 |
| 5705 |
| 5821 |
| 5907 |
| 6880 |
| 6920 |
| 6946 |
| 7472 |
| 7566 |
| 7935 |
| 8432 |
| 10347 |
| 10838 |
| 11372 |
| 12960 |

Using a cutoff of 0.2 for A, the combination with the most passing features was deemed the most similar and used for batch correction purposes. In the case of a tie, the combination sitting in the leftmost position of the prescribed ordered 1_5, 1_6, 2_5, 2_6 is used. If a combination was not found where at a minimum 15 of the 20 features passed the cutoff for a batch, then the batch would be considered a failure and would need to be re-run. In this project, all 3 batches passed using these criteria. For each batch, the combination of most similar reference spectra replicates was found. An average was created from the two replicates by averaging the feature values of the two replicates for each feature. These average feature values were used as the reference for each batch for the purpose of batch correction.

E. Batch Correction

Batch 1 was used as the baseline batch to correct all other batches. The reference sample was used to find the correction coefficients for each of the batches 2 and 3 by the following procedure.

Within each batch j (2≤j≤3), the ratio $$\hat{r}_i^j = \frac{A_i^j}{A_i^1}$$

and the average amplitude $$\overline{A}_i^j = \frac{1}{2}(A_i^j + A_i^1)$$

are defined for each $i^{th}$ feature centered at $(m/z)_i$, where $A_j^i$ is the average reference spectrum amplitude of feature i in the batch being corrected and $A_i^1$ is the reference spectrum amplitude of feature i in batch 1 (the reference standard). It is assumed that the ratio of amplitudes between two batches follows the dependence $$r(\overline{A},(m/z))=(a_0+a_1\ln(\overline{A}))+(b_0+b_1\ln(\overline{A}))(m/z)+c_0(m/z)^2.$$

On a batch to batch basis, a continuous fit is constructed by minimizing the sum of the square residuals, $\Delta^j=\Sigma_i(\hat{r}_i^j-r^j(a_0, a_1, b_0, b_1, c_0))^2$, and using the experimental data of the reference sample. The features used to create this fit are only a subset (described in Appendix C, table C.1, of our prior provisional application, incorporated by reference) of the whole available set, from which features known to be have poor reproducibility were removed. Steps were taken to not include outlier points in order to avoid bias in the parameter estimates. The values of the coefficients $a_0$, $a_1$, $b_0$, $b_1$ and $c_0$, obtained for the different batches are listed in Appendix C of the prior provisional application (table C.2). The projection in the $\hat{r}_i^j$ versus $(m/z)_i$ plane of the points used to construct the fit for each batch of reference spectra, together with the surface defined by the fit itself, is shown in figure C.1 of Appendix C of our prior provisional application.

Once the final fit, $r^j(\overline{A},(m/z))$, is determined for each batch, the next step is to correct, for all the samples, all the features (with amplitude A at (m/z)) according to $$A_{corr}=\frac{A}{r^j(A,(m/z))}.$$

After this correction, the corrected $(A_i^j,(m/z)_i,\hat{r}_i^j)$ feature values calculated for reference spectra lie around the horizontal line defined by r=1, as shown in figure C.2 of Appendix C of our prior provisional application.

The mass spectrometry data set (feature table) for each of the blood-based samples and resulting from the above pre-processing steps is referred to as development sample set 100 in FIG. 1 and was used to construct a number of different classifiers. The process of using this development sample set to generate classifiers will be described in the following section.

CMC/D Classifier Generation Method

The new classifier development process using the method of combination of mini-classifiers (mCs) with dropout (CMC/D) is shown schematically in FIG. 1. The steps in this process are explained in detail below. The methodology, its various advantages, and several examples of its use, are explained in great detail in U.S. patent application Ser. No. 14/486,442 filed Sep. 15, 2014, the content of which is incorporated by reference. A brief explanation of the methodology will be provided here first, and then illustrated in detail in conjunction with FIG. 1 for the generation of the MDS prognosis classifiers.

In contrast to standard applications of machine learning focusing on developing classifiers when large training data sets are available, the big data challenge, in bio-life-sciences the problem setting is different. Here we have the problem that the number (n) of available samples, arising typically from clinical studies, is often limited, and the number of attributes (p) per sample usually exceeds the number of samples. Rather than obtaining information from many instances, in these deep data problems one attempts to gain information from a deep description of individual instances. The present methods take advantage of this insight, and are particularly useful, as here, in problems where p>>n.

The method includes a first step a) of obtaining measurement data for classification from a multitude of samples, i.e., measurement data reflecting some physical property or characteristic of the samples. The data for each of the samples consists of a multitude of feature values, and a class label. In this example, the data takes the form of mass spectrometry data, in the form of feature values (integrated peak intensity values at a multitude of m/z ranges or peaks) as well as a label indicating some attribute of the sample (patient Early or Late death). In this example, the class labels were assigned by a human operator to each of the samples after investigation of the clinical data associated with the sample. The development sample set is then split into a training set and a test set and the training set is used in the following steps b), c) and d).

The method continues with a step b) of constructing a multitude of individual mini-classifiers using sets of features from the samples up to a pre-selected feature set size s (s=integer 1 . . . n). For example a multiple of individual mini- or atomic classifiers could be constructed using a single feature (s=1), or pairs of features (s=2), or three of the features (s=3), or even higher order combinations containing more than 3 features. The selection of a value of s will normally be small enough to allow the code implementing the method to run in a reasonable amount of time, but could be larger in some circumstances or where longer code run-times are acceptable. The selection of a value of s also may be dictated by the number of measurement data values (p) in the data set, and where p is in the hundreds, thousands or even tens of thousands, s will typically be 1, or 2 or possibly 3, depending on the computing resources available. The mini-classifiers execute a supervised learning classification algorithm, such as k-nearest neighbors, in which the values for a feature or pairs of features of a sample instance are compared to the values of the same feature or features in a training set and the nearest neighbors (e.g., k=5) in an s-dimensional feature space are identified and by majority vote a class label is assigned to the sample instance for each mini-classifier. In practice, there may be thousands of such mini-classifiers depending on the number of features which are used for classification.

The method continues with a filtering step c), namely testing the performance, for example the accuracy, of each of the individual mini-classifiers to correctly classify at least some of the multitude of samples, or measuring the individual mini-classifier performance by some other metric (e.g. the difference between the Hazard Ratios (HRs) obtained between groups defined by the classifications of the individual mini-classifier for the training set samples) and retaining only those mini-classifiers whose classification accuracy, predictive power, or other performance metric, exceeds a pre-defined threshold to arrive at a filtered (pruned) set of mini-classifiers. The class label resulting from the classification operation may be compared with the class label for the sample known in advance if the chosen performance metric for mini-classifier filtering is classification accuracy. However, other performance metrics may be used and evaluated using the class labels resulting from the classification operation. Only those mini-classifiers that perform reasonably well under the chosen performance metric for classification are maintained. Alternative supervised classification algorithms could be used, such as linear discriminants, decision trees, probabilistic classification methods, margin-based classifiers like support vector machines, and any other classification method that trains a classifier from a set of labeled training data.

To overcome the problem of being biased by some univariate feature selection method depending on subset bias, we take a large proportion of all possible features as candidates for mini-classifiers. We then construct all possible KNN classifiers using feature sets up to a pre-selected size or depth (parameter s). This gives us many "mini-classifiers": e.g. if we start with 100 features for each sample (p=100), we would get 4950 "mini-classifiers" from all different possible combinations of pairs of these features (s=2), 161,700 mini-classifiers using all possible combination of three features (s=3), and so forth. Other methods of exploring the space of possible mini-classifiers and features defining them are of course possible and could be used in place of this hierarchical approach. Of course, many of these "mini-classifiers" will have poor performance, and hence in the filtering step c) we only use those "mini-classifiers" that pass predefined criteria. These criteria are chosen dependent on the particular problem: If one has a two-class classification problem, one would select only those mini-classifiers whose classification accuracy exceeds a pre-defined threshold, i.e., are predictive to some reasonable degree. Even with this filtering of "mini-classifiers" we end up with many thousands of "mini-classifier" candidates with performance spanning the whole range from borderline to decent to excellent performance.

The method continues with step d) of generating a master classifier by combining the filtered mini-classifiers using a regularized combination method. In one embodiment, this regularized combination method takes the form of repeatedly conducting a logistic training of the filtered set of mini-classifiers to the class labels for the samples. This is done by randomly selecting a small fraction of the filtered mini-classifiers as a result of carrying out an extreme dropout from the filtered set of mini-classifiers (a technique referred to as drop-out regularization herein), and conducting logistical training on such selected mini-classifiers. While similar in spirit to standard classifier combination methods (see e.g. S. Tulyakov et al, Review of Classifier Combination Methods, Studies in Computational Intelligence, Volume 90, 2008, pp. 361-386), we have the particular problem that some "mini-classifiers" could be artificially perfect just by random chance, and hence would dominate the combinations. To avoid this overfitting to particular dominating "mini-classifiers", we generate many logistic training steps by randomly selecting only a small fraction of the "mini-classifiers" for each of these logistic training steps. This is a regularization of the problem in the spirit of dropout as used in deep learning theory. In this case, where we have many mini-classifiers and a small training set we use extreme dropout, where in excess of 99% of filtered mini-classifiers are dropped out in each iteration.

In more detail, the result of each mini-classifier is one of two values, either "Early" or "Late" in this example. We can then use logistic regression to combine the results of the mini-classifiers in the spirit of a logistic regression by defining the probability of obtaining an "Early" label via standard logistic regression (see e.g. the Wikipedia page on logistic regression).

$$P(\text{"Early"}|\text{feature for a spectrum}) = \frac{\exp\left(\sum_{mini\ classifiers} w_{mc} I(mc(\text{feature values}))\right)}{\text{Normalization}}$$

Eq. (1)

where $I(mc(\text{feature values}))=1$, if the mini-classifier mc applied to the feature values of a sample returns "Early", and 0 if the mini-classifier returns "Late". The weights for each of the miniClassifiers, $w_{mc}$, are unknown and need to be determined from a regression fit of the above formula for all samples in the training set using +1 for the left hand side of the formula for the Early-labeled samples in the training set, and 0 for the Late-labeled samples, respectively. As we have many more mini-classifiers, and therefore weights, than samples, typically thousands of mini-classifiers and only tens of samples, such a fit will always lead to nearly perfect classification, and can easily be dominated by a mini-classifier that, possibly by random chance, fits the particular problem very well. We do not want our final test to be dominated by a single special mini-classifier which only performs well on this particular set and is unable to generalize well. Hence we designed a method to regularize such behavior: Instead of one overall regression to fit all the weights for all mini-classifiers to the training data at the same, we use only a few of the mini-classifiers for a regression, but repeat this process many times in generating the master classifier. For example we randomly pick three of the mini-classifiers, perform a regression for their three weights, pick another set of three mini-classifiers, and determine their weights, and repeat this process many times, generating many random picks, i.e. realizations of three mini-classifiers. The final weights defining the CMC/D master classifier are then the averages of the weights over all such realizations. The number of realizations should be large enough that each mini-classifier is very likely to be picked at least once during the entire process. This approach is similar in spirit to "drop-out" regularization, a method used in the deep learning community to add noise to neural network training to avoid being trapped in local minima of the objective function.

Other methods for performing the regularized combination in step (d) that could be used include:

Logistic regression with a penalty function like ridge regression (based on Tikhonov regularization, Tikhonov, Andrey Nikolayevich (1943). "Об устойч ивости обрат ных задач" [On the stability of inverse problems]. Doklady Akademii Nauk SSSR 39 (5): 195-198.)

The Lasso method (Tibshirani, R. (1996). Regression shrinkage and selection via the lasso. J. Royal. Statist. Soc B., Vol. 58, No. 1, pages 267-288).

Neural networks regularized by drop-out (Nitish Shrivastava, "Improving Neural Networks with Dropout", Master's Thesis, Graduate Department of Computer Science, University of Toronto; available on line from the computer science department website of the University of Toronto, link set forth in on prior provisional application.

General regularized neural networks (Girosi F. et al, Neural computation, (7), 219 (1995)).

The above-cited publications are incorporated by reference herein. Our approach of using drop-out regularization has shown promise in avoiding over-fitting, and increasing the likelihood of generating generalizable tests, i.e. tests that can be validated in independent sample sets.

In step e) of the method, the set of samples are randomly separated into a test set and a training set, and the steps b)-d) are repeated in the programmed computer for different realizations of the separation of the set of samples into test and training sets, thereby generating a plurality of master classifiers, one for each realization of the separation of the set of samples into training and test sets.

The method continues with step f) of defining a final classifier from one or a combination of more than one of the plurality of master classifiers. In the present example, the final classifier is defined as a majority vote of all the master classifiers resulting from each separation of the sample set into training and test sets, and if the sample is in the development set, the majority vote of all the master classifiers resulting from each separation of the sample set into training and test when the sample is not in the training set.

With reference now to FIG. 1, we have a development sample set 100, in this case the mass spectrometry data of the patients provided in the study.

Step 102 Definition of Initial Class Labels

For the purposes of developing a prognostic classifier able to identify patients with better or worse survival after presentation with MDS, the initial class labels were assigned based on short or long survival (class label "Early"=early death, class label "Late"=long survival), with the "Early" group 104 initially composed of patients with death or censoring at or before 24 months and the "Late" group 106 composed of patients with death or censoring after 24 months. Only the 101 patients with survival data available were used in this classifier development approach.

Steps 120, 122 Creation and Filtering of Mini-Classifiers

Once the initial definition of the class labels has been established, the development set (100) is split into training and test sets at step 108. In step 120, many k-nearest neighbor (kNN) mini-classifiers (mCs) that use the training set as their reference set are constructed using subsets of features from the 318 mass spectral features identified (see Appendix A). For many of the investigations all possible single features and pairs of features were examined (s=2); however, when fewer features were used, triplets were also considered (s=3). For the 318 mass spectral features, just traversing all single features and pairs of features amounts to considering 50,721 possible mCs. The parameters used to traverse the space of mCs for this project are listed in table 8.

TABLE 8

Parameters used to create mCs

| kNN parameters | |
| --- | --- |
| k | 5 (except when otherwise indicated) |

Furthermore, we used all pairs of features and all single features for "2-deep" mini-classifiers (s=2), and all single features, all pairs of features and all triples of features for "3-deep" mini-classifiers (s=3).

At step 126, to target a final classifier that has certain performance characteristics, these mCs are filtered. Each mC is applied to its training set (112) and performance metrics are calculated from the resulting classifications of the training set. Only those mCs that satisfy thresholds on these performance metrics pass filtering to be used further in the process. The mCs that fail filtering are discarded. For this project, hazard ratio filtering was used, i.e. the classifier was applied to a set of samples (such as the training set or a subset of the patients without liver disease) and the hazard ratio for survival between the groups defined by the resulting classification had to lie within a preset range for the mC to pass filtering. The filtering options used in this project are listed in Table 9. We also tried accuracy filtering and found it produced inferior results.

Step 130 and 132 Master Classifier as a Combination of Mini-Classifiers Using Logistic Regression with Dropout Once the filtering of the mCs is complete, the mCs are combined in one master classifier (MC) using a logistic regression trained using the training set labels. To help avoid overfitting the regression is regularized using extreme drop out. Most of the CMC/D approaches in this study randomly selected 10 of the mCs for inclusion in each logistic regression iteration. The number of dropout iterations was selected based on the typical number of mCs passing filtering for each approach to ensure that each mC was likely to be included within the drop out process multiple times.

Step 134 Analysis of Master Classifier Performance and Training and Test Splits (Loop 135)

At step 134, the performance of the MC generated at step 130 is then tested by subjecting the test set split (110) to classification by the MC. The performance of the MC is then evaluated at step 134.

The split of the class groups into training and test sets at step 108 is performed many times using a stratified randomization, as indicated by the loop 135. Each training/test split produces a MC which can be applied to the split test set (110) at step 134 to assess performance. The use of multiple training/test splits avoids selection of a single, particularly advantageous or difficult, training set for classifier creation and avoids bias in performance assessment from testing on a test set that could be especially easy or difficult to classify.

One other advantage of these multiple training/test splits is that it allows for the refinement of the initial assignment for the class groups ("Early"/"Late") when these are not known definitively. For example, when one tries to split a patient cohort into two groups with better ("Late") and worse ("Early") time-to-event outcome, it is generally not clear, a priori, which patients will be in which class, as each class will typically display a range of outcomes and these usually overlap. (That is, it is very likely that there are patients in the "Early" group who have longer time-to-event values than some patients in the "Late" group.) When the class definitions are uncertain, the CMC/D approach as shown in FIG. 1 allows one to make an initial guess for the class label assignments (at step 102) and then refine this through a series of iterations of the process (see FIG. 1, loop 142).

At step 136, the classifier performance data is analyzed for each training/test set split, which is performed by obtaining performance characteristics for the MCs for each training/test set split and the classification results.

As indicated at 140, a check is made to see if any samples persistently misclassify and if so those samples that persistently misclassify have their class label flipped (Early→Late; Late→Early) and the process repeats as indicated by loop 142.

In particular, for the training/test splits where a particular sample from the defined groups (102), i.e. the union of samples in Class 1 (Early) (104) and Class 2 (Late) (106) is in the test set (110), the resulting classifications for the sample can be obtained by applying the respective MCs. If the sample persistently misclassifies relative to the initial guess for patient prognosis class, the sample can be moved from the better outcome class into the worse outcome class, or vice versa. Carrying out this procedure of checking the classifications and flipping the class when there are persistent misclassifications for all samples with defined class labels (102) produces a new, refined version of the group definitions which is the starting point for a second iteration of the CMC/D process as indicated by loop 142 looping back to step 102. This refinement process can be iterated so that the better/worse prognosis classes are determined at the same time as a classifier is constructed. Each approach to this project based on survival outcome involved several rounds of these reference class label swaps.

The output of the logistic regression that defines each MC generated at step 130 is a probability of being in one of the two training classes. These MC outputs can be combined to make one resultant classifier in several ways.

Applying a cutoff (e.g. 0.5) to these probabilities, one can generate a binary classification label for a sample from each MC. These labels can then be combined in a majority vote to obtain one binary classification for a sample. When analyzing the performance of the classifier in the development set (at step 134, 138), it is helpful to use a modified majority vote for samples which are used in training the classifier. For samples which are used in the training set of some of the training/test set split realizations, the modified majority vote (MMV) is defined as the majority vote of the MC labels over the MCs which do not have the sample in the training set. For samples which are never used in any training set, the modified majority vote and majority vote are identical.

The MC probabilities can be averaged to yield one average probability for a sample. When working with the development set, this approach can also be adjusted to average over MCs for which a given sample is not included in the training set, in an analogous way to the MMV procedure. These average probabilities can be used as the output of a classifier or a threshold can be applied to convert them into a binary classification.

The present CMC/D method works best when the two classes in the training set are of approximately equal sizes. To achieve this it may be necessary to sample the classes at different rates. In addition, performance has been seen to deteriorate quickly when the size of the training sets drops very low. When there are small numbers in one of the training classes, it can be advantageous to include most of the samples in the kNN reference set in each realization, leaving only a few samples as a test set. This process still works well providing the number of training/test set split realizations is scaled up to allow for adequate statistics for all samples when they are in the test sets of the realizations.

Many implementations of the CMC/D process were investigated, varying in the population used for the test/training splits, the filtering used in the CMC/D process, and the feature space explored.

Some of these approaches involved feature selection within the sets of mass spectral features, which was done by choosing the features with the lowest p-values for a t-test between the two class definitions for each round of CMC/D.

A summary of some of the approaches tried during new classifier development using the standard CMC/D workflow and the first set of defined features is presented in Table 9. Table 9 summarizes the approaches that made classifiers based on better and worse survival.

TABLE 9

Approaches to CMC/D used for identification of classifier based on better or worse survival

| Patient subset | Features Used | Depth (# features in kNN mCs) s | Filtering Options (default k = 5) |
|---|---|---|---|
| All patients with survival data (n = 101) | 318 | 2 | 0.75 < training set accuracy < 0.95 |
| | 318 | 2 | 3 < HR < 10 |
| | 100 selected by t-test | 2 | 3 < HR < 10 |
| | 100 selected by t-test | 2 | 3 < HR <10 with sCD44 and sEcad as features |
| | 100 selected by t-test | 2 | 3 < HR < 10 run with k = 9 |
| RA patients with survival data (n = 45) | 100 selected by t-test | 2 | 3 < HR < 10 |
| RAEB patients with survival data (n = 26) | 100 selected by t-test | 2 | 3 < HR < 10 |

Note that we explored generation of classifiers with either 100 or all 318 of the features listed in Appendix A. It would be possible to use other numbers of features, e.g., selected from t-statistic or selected by some other statistical method for classification power, such as 50, 150 or some other number of features. Preferably at least 50 features are used in order to take advantage of the deep spectral information obtained by subjecting the samples to at least 100,000 laser shots.

Results

Figure 3A:
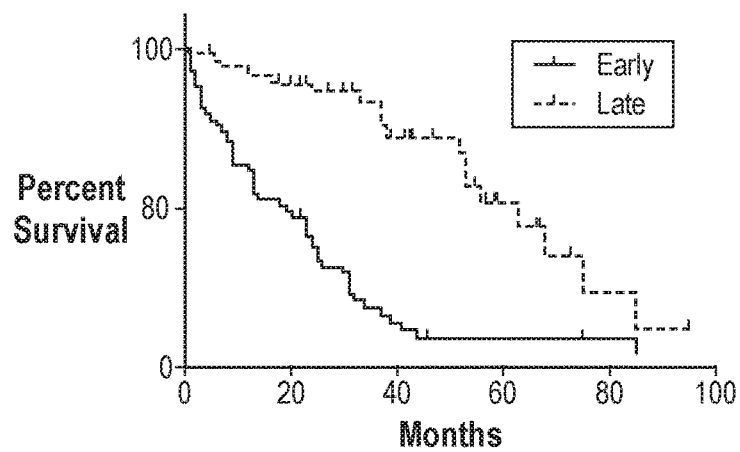
Figure 3B:
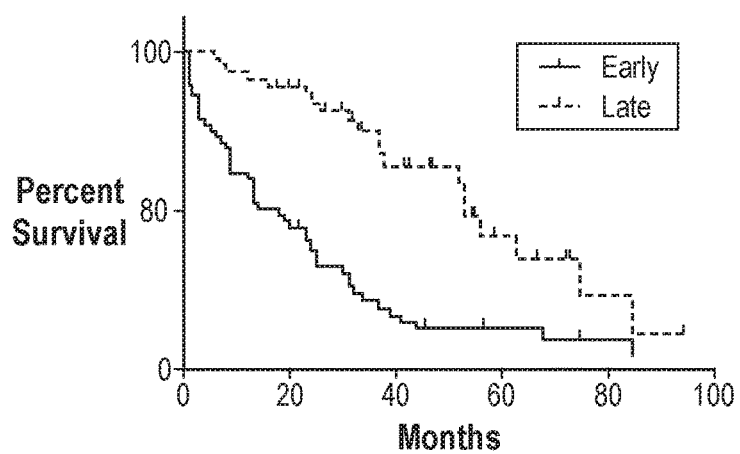
Figure 3C:
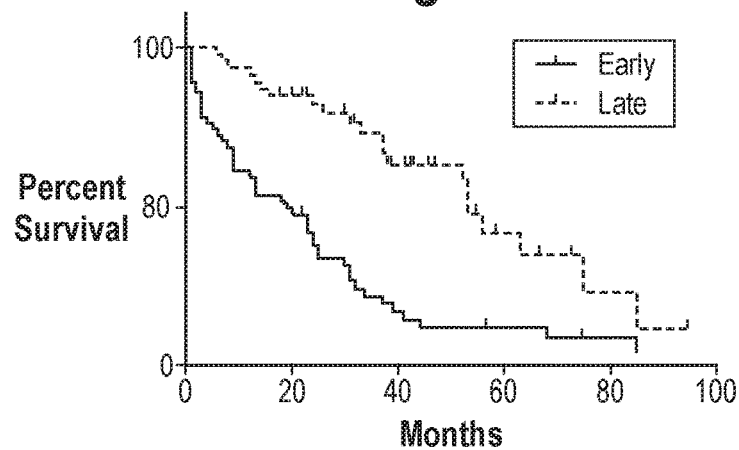
Figure 3F:
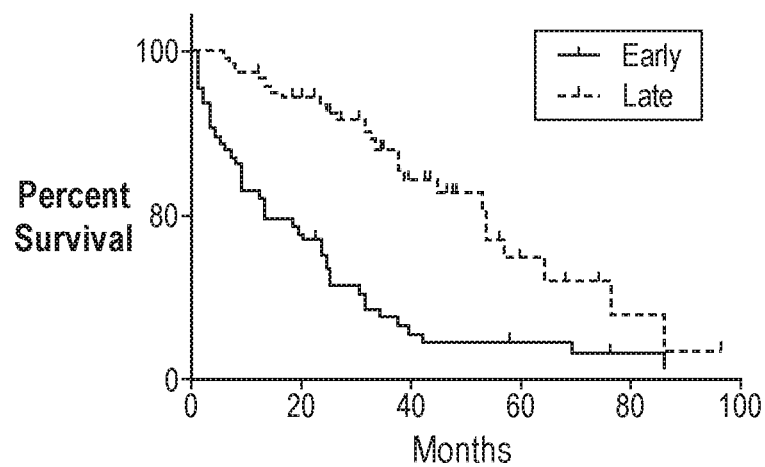

The performance of the classifiers based on better or worse survival was assessed using the Kaplan-Meier survival curves for the resulting classifications as defined by modified majority vote (out of bag estimate). For this problem, the best classifier performance was obtained using the subset of 100 features of Appendix A selected based on lowest p value from a t-test between the initial class definitions of Early (poor prognosis) and Late (good prognosis). FIG. 3 shows the Kaplan-Meier plots for the survival of Early and Late groups along the iterations of the CMC/D process as the class definitions are refined during successive iterations of loop 142. All patients with survival data and MDS (RA, RAEB, RARS or CMML) are included. The panel FIG. 3F shows the result at convergence of the class labels and is the result expected to generalize best to unseen sample sets. For this approach K in the K-nearest neighbor algorithm=5 and hazard ratio filtering of mCs were used. Note that in the figures the plots show a clear separation of survival curves between the patients in the Early and Late groups.

For the final classifier (FIG. 3F) the hazard ratio between Early and Late groups is 0.34 with 95% confidence interval (CI) of 0.18-0.49, log-rank p value<0.001. The median survival is 13 months (95% CI: 9-24 months) in the Early group compared with 53 months (95% CI: 37-75 months) in the Late group. The classifications assigned to each sample are listed in Appendix D of our prior provisional application. We explored generating classifiers that used larger values of K in the KNN algorithm used by the mC in FIG. 1, and classifiers using accuracy filtering instead of hazard ratio filtering in step 126 of FIG. 1, but both approaches produced inferior results.

Figure 4:
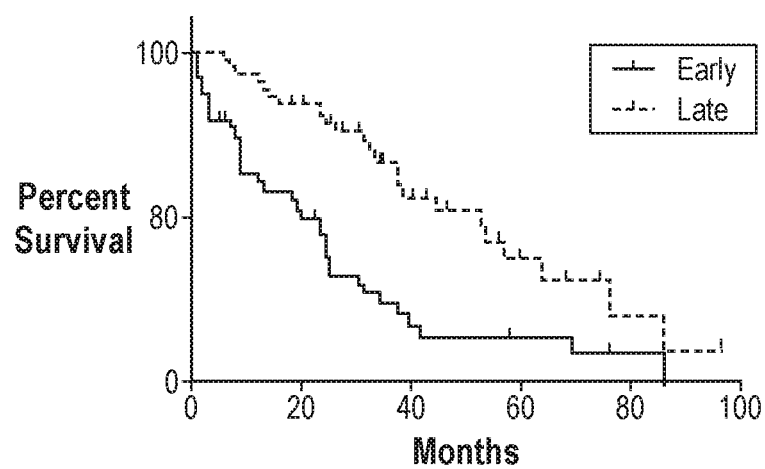
FIG. 4 is a Kaplan-Meier plot for survival for patients with either RA, RAEB or RARS by prognostic classification label, Early or Late, assigned with the same final classifier associated with the Kaplan-Meier plot of FIG. 3F.

As patients classified with CMML (see Table 1) are now sometimes no longer classified as having MDS, the final classifier of FIG. 3F was also analyzed within the subset of patients with only RA, RAEB or RARS. The result is shown in FIG. 4. This figure also shows the clear separation in the survival curves between the Early and Late groups. Within this patient population the hazard ratio between Early and Late groups is 0.37 (95% CI: 0.19-0.57), log-rank p value<0.001. The median survival is 23 months in the Early group compared with 52 months in the Late group. The distribution of Early and Late groups by FAB classification is shown in table 10.

TABLE 10

Distribution of Early and Late groups by FAB classification (all patients with or without survival data)

| FAB classification | Early | Late |
| --- | --- | --- |
| AML | 5 | 1 |
| RAEB-t | 9 | 8 |
| CMML | 11 | 6 |
| RA | 20 | 26 |
| RAEB | 17 | 12 |
| RARS | 7 | 7 |
| Healthy | 9 | 10 |

NB: the fact that some of the healthy patients were classified as Early could be due to a variety of factors, including a) we could be measuring something that could also be present in non-MDS patients, for example the level at which a person's immune system functions; and b) the feature values of healthy patients are so different compared to the rest of the training set that when you try to classify a healthy patient you get essentially a random answer back because the features lie way off in feature space compared with the MDS patients, and so asking which MDS patient is a nearest neighbor is practically meaningless and the result more or less random.

Possible correlations between the classifier labels, Early and Late, and known prognostic factors, such as IPSS score and karyotype were investigated. The breakdown of Early and Late groups by other prognostic factors is shown in table 11.

TABLE 11

Distribution of Early and Late groups by other prognostic factors (patients with RA, RAEB, CMML, RARS and survival data only, i.e. the population in the Kaplan-Meier plots)

| Factor | | Early group (N = 51) | Late group (N = 50) | P value |
| --- | --- | --- | --- | --- |
| IPSS Score | 0 | 11 | 24 | 0.002* |
|  | 0.5 | 13 | 10 |  |
|  | 1.0 | 14 | 9 |  |
|  | 1.5 | 4 | 0 |  |
|  | 2.0 | 5 | 0 |  |
|  | 2.5 | 0 | 2 |  |
| IPSS Score | Low risk | 11 | 24 | <0.001* |
|  | Intermediate 1 risk | 27 | 19 |  |
|  | Intermediate 2 risk | 9 | 0 |  |
|  | High risk | 0 | 2 |  |
| Genetic Category | Poor | 7 | 0 | 0.060* |
|  | Del5 | 8 | 9 |  |
|  | intermediate | 6 | 6 |  |
|  | Good | 23 | 25 |  |
| Age | median | 70 | 72 | 0.676ˆ |
|  | mean | 68.8 | 67.6 | 0.658 ˣ |
|  | range | 38-93 | 19-86 |  |

TABLE 11-continued

Distribution of Early and Late groups by other prognostic factors (patients with RA, RAEB, CMML, RARS and survival data only, i.e. the population in the Kaplan-Meier plots)

| Factor | | Early group (N = 51) | Late group (N = 50) | P value |
| --- | --- | --- | --- | --- |
| sCD44 § | median | 707 | 530 | <0.001ˆ |
|  | mean | 973 | 558 | 0.009 ˣ |
|  | range | 301-7961 | 340-978 | <0.001* |
|  | High | 22 | 3 |  |
|  | Low | 29 | 47 |  |

*Fisher's exact test;
ˆMann-Whitney test;
ˣt-test

§ sCD44 is the serum biomarker described in Loeffler-Ragg J., et al., *Serum CD44 levels predict survival in patients with low-risk myelodysplastic syndromes* Crit. Rev. Oncol. Hematol. vol. 78 no. 2 pp. 150-61 (2011)

There are significant correlations between Early and Late groups with IPSS score or a trend to significance with gene category. There is also a strong correlation between sCD44 category (high versus low) and Early or Late label.

To investigate any independent prognostic significance of the Early and Late classification labels, further analysis was carried out using Cox proportional hazards models stratified by FAB category. As a univariate factor in this stratified analysis, Early/Late classification is highly significant with hazard ratio 0.30 (95% CI: 0.18-0.51), p<0.001. In multivariate analysis, the classification labels of Early and Late remain significant predictors of outcome, even when adjusted for IPSS score and genetic category (hazard ratio=0.40 (95% CI: 0.21-0.74), p=0.004). IPSS score and "bad" karyotype gene classification are also simultaneously significant predictors of survival. On adjustment by sCD44 category, as defined in Loeffler-Ragg et al: (see above-cited paper), either of Early/Late classification alone or of the combination of Early/Late classification, IPSS score, and genetic classification, Early/Late label remains an independent predictor of survival. These results indicate that, despite the clear correlations between Early/Late label and other prognostic factors, the Early/Late label is a significant predictor of survival independent of other prognostic factors. Further details of the multivariate analyses are included in Appendix E in our prior provisional application, incorporated by reference.

Figure 5C:
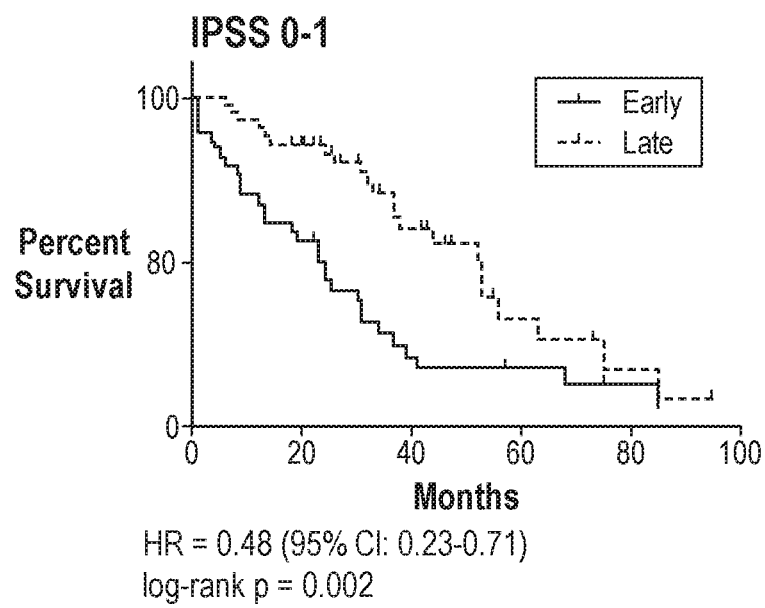
Figure 5D:
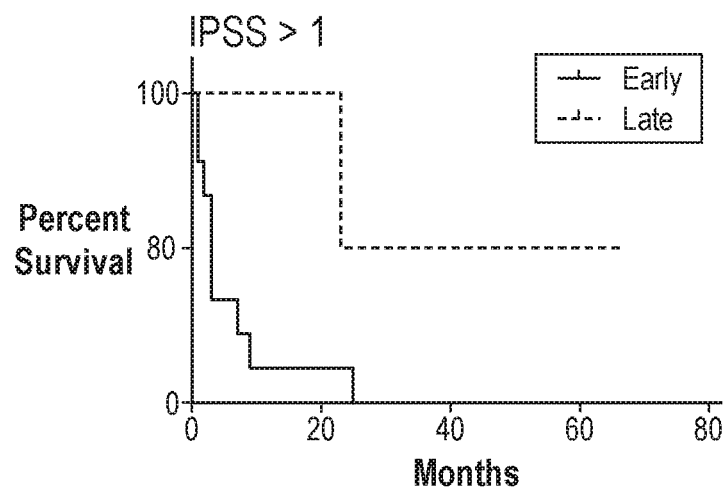
Figure 5E:
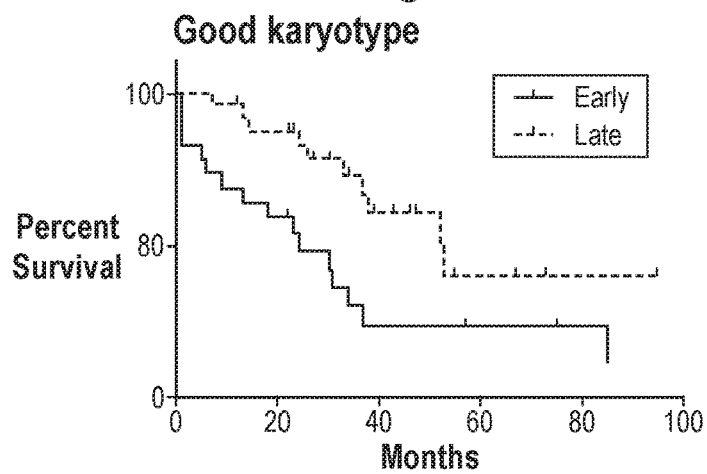
Figure 5F:
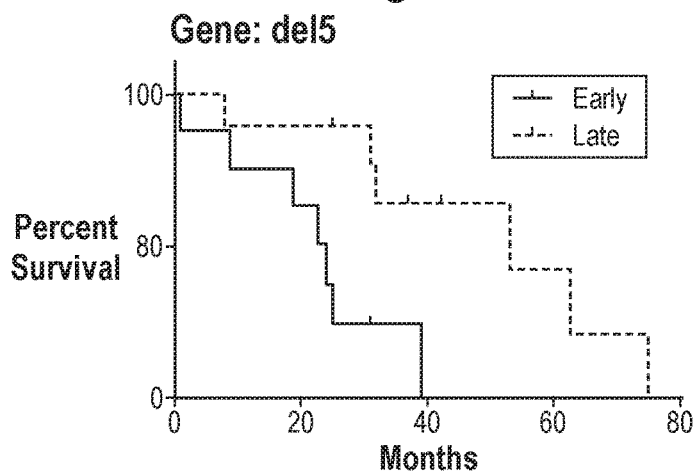
Figure 5G:
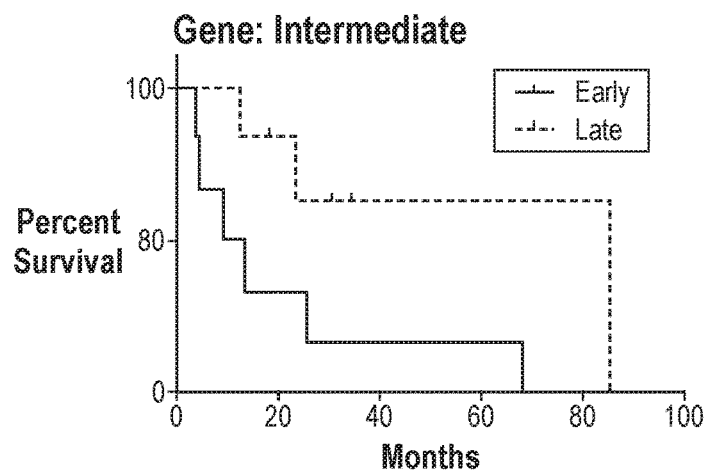
Figure 5H:
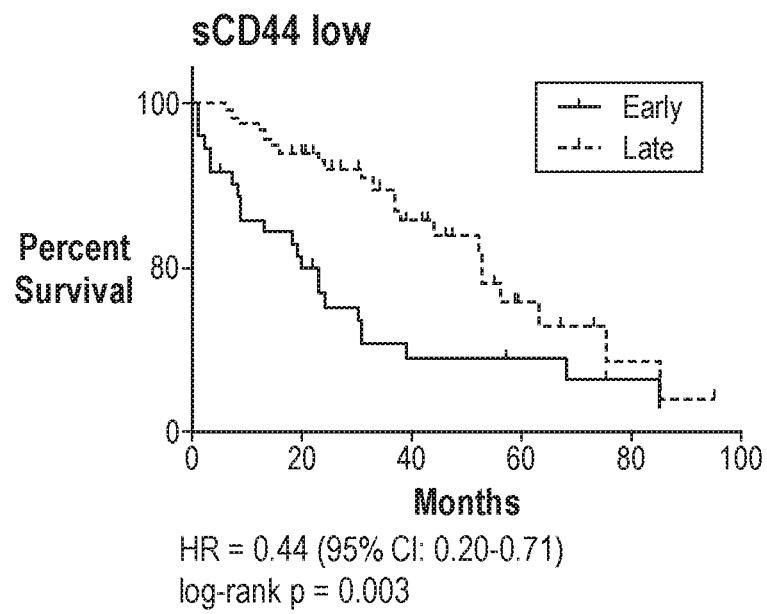
Figure 5I:
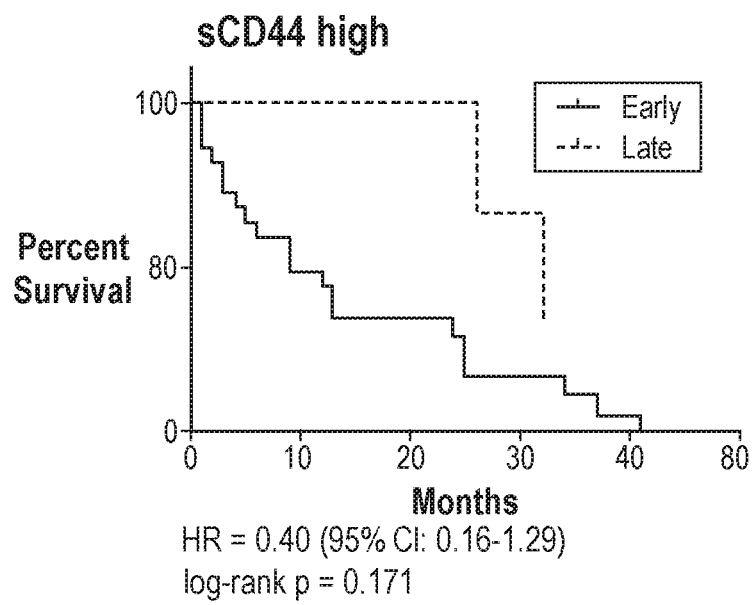

Subgroup analyses supported these conclusions that Early/Late label provides prognostic information additional and complementary to other existing, available prognostic factors. Kaplan-Meier plots of survival for various subgroups by Early and Late classification are shown in FIG. 5. FIG. 5A shows the plot for the patients with IPSS score of 0, FIG. 5B shows the plot for the patients with IPSS score of 0.5-1, FIG. 5C shows the plot for the patients with IPSS score of between 0 and 1; FIG. 5D shows the plot for the patients with IPSS score>1; FIG. 5E shows the plot for "Good karyotype" patients; FIG. 5F shows the plot for "Gene: del5" patients; FIG. 5G shows the plot for "Gene: Intermediate" patients; FIG. 5H shows the plot for biomarker "sCD44 low" patients, and FIG. 5I shows the plot for biomarker "sCD44 high" patients. Note that in all of these plots, there is a clear separation of the survival curves for Early and Late labeled patients.

It is apparent from FIGS. 5A-5I that the classifier label is able to stratify IPSS low risk patients (FIG. 5C) and although there are very few IPSS high risk patients with Late classification, they have relatively very good outcomes (FIG. 5D). Within the gene-defined subtypes good, del5 and intermediate, the Early subgroup has inferior outcomes to that of the Late subgroup. The bad karyotype group only contains patients classified to the Early group (Kaplan-Meier plot for this subgroup not shown).

While there was strong correlation between Early and Late classifications and sCD44 level, the classification Early and Late still clearly stratifies the sCD44 low group (see FIG. 5H), therefore the classification label Early or Late adds additional information to that obtained solely from a sCD44 test. Only three patients in the sCD44 high group are classified as Late (FIG. 5I) and these all have survival of at least 26 months.

Figure 6A:
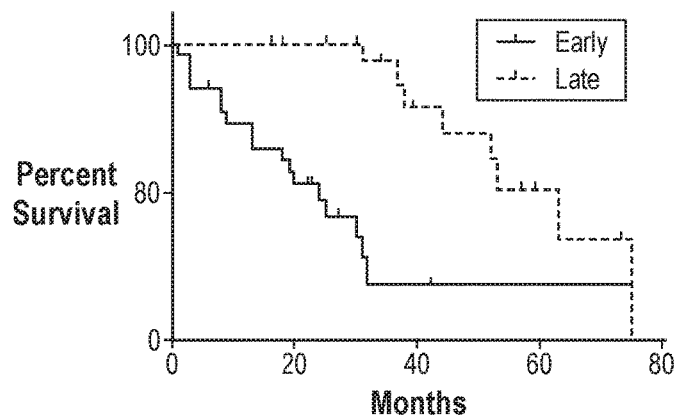
FIGS. 6A-6F are Kaplan-Meier plots for survival for MDS patients with RA according to classifier label, Early or Late. The results are shown at each stage of the class label refinement process (successive iterations of loop 142 in FIG. 1). The final classifier result is shown in panel FIG. 6E, and the last panel FIG. 6F compares the results for this classifier with the stratification obtained from the classifications for the RA samples from the classifier trained on all MDS samples (performance results shown in FIG. 3).
Figure 6B:
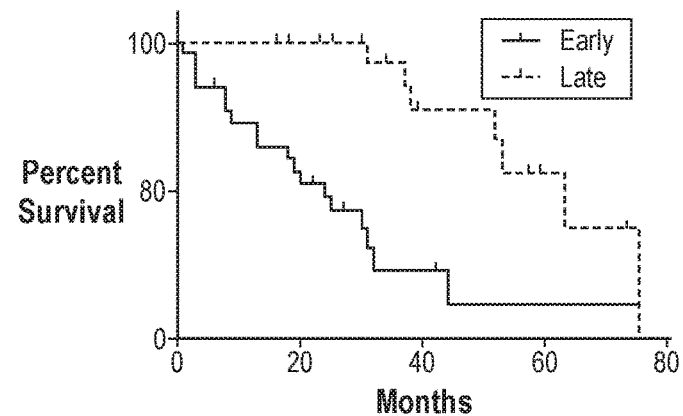
Figure 6C:
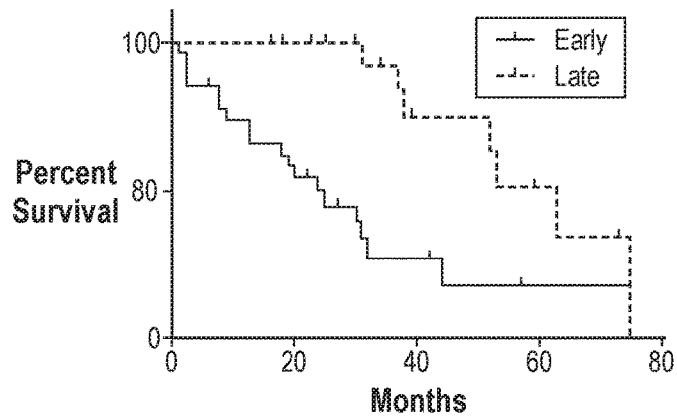
Figure 6D:
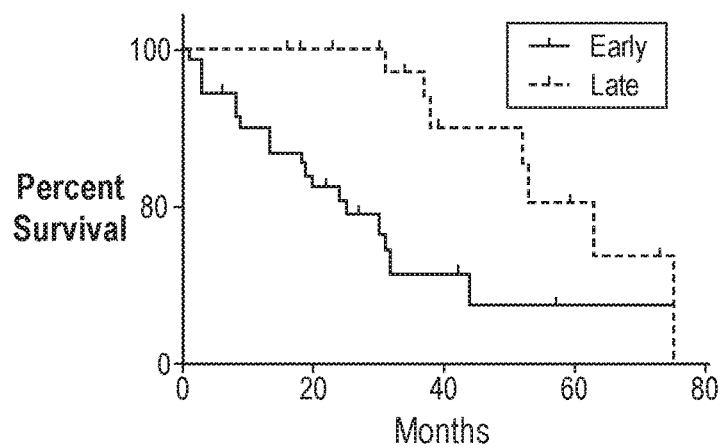
Figure 6E:
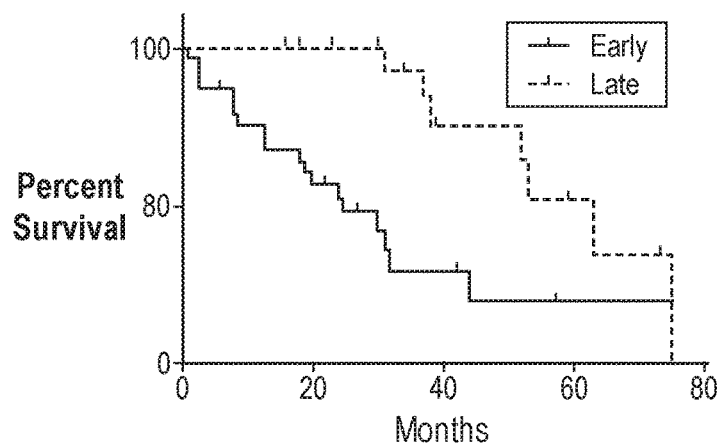
Figure 6F:
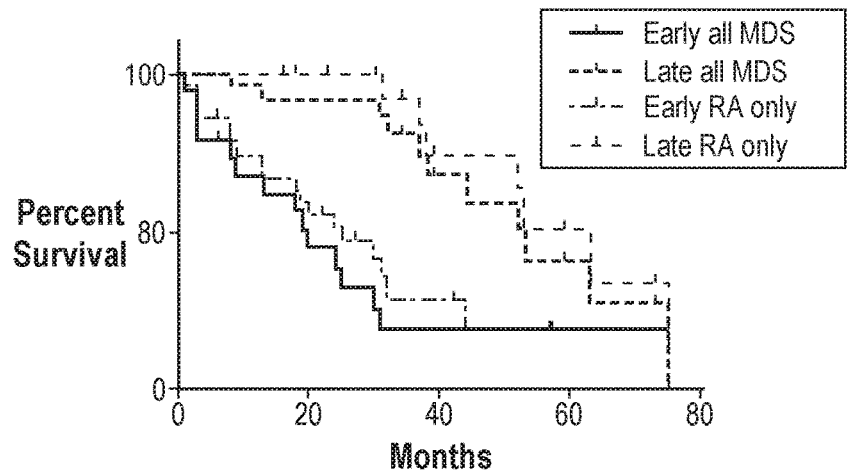

In addition to creating classifiers trained on patients in all MDS subgroups, separate classifiers were also developed using the same methodology within the two largest MDS subgroups, RA and RAEB (see Table 1 definition). The results from each refinement of class labels are shown for the RA classifier in FIG. 6 and for the RAEB classifier in FIG. 7. In particular, FIGS. 6A-6F are Kaplan-Meier plots for survival for MDS patients with RA according to classifier label, Early or Late. The results are shown at each stage of the class label refinement process (successive iterations of loop 142 in FIG. 1). The final classifier result is shown in panel FIG. 6E, and the last panel FIG. 6F compares the results for this classifier with the stratification obtained from the classifications for the RA samples from the classifier trained on all MDS samples (shown in FIG. 3).

For the final RA classifier (FIG. 6E) the hazard ratio between Early and Late groups is 0.32 (95% CI: 0.14-0.67), log-rank p value 0.005. The median survival is 25 months (95% CI: 13-32 months) in the Early group compared with 63 months (95% CI: 37-75 months) in the Late group. There are no patient deaths in the Late group before 30 months, by which time patient survival in the Early group is less than 50%. The classifications assigned to each RA sample by this classifier are listed in Appendix D of our prior provisional application which is incorporated by reference. The final panel FIG. 6F compares the classifications obtained for the RA samples between this classifier and the classifier trained on the set of all MDS samples. Although the difference between the two classifiers is not great, the RA-developed classifier assigns fewer patients to the Late group; in particular two relatively early events and some patients who are censored at early times are in the Late group for the all MDS classifier, but the Early group for the RA classifier. Hence, the RA classifier may be preferable in this subgroup for identifying very good prognosis patients.

Figure 7A:
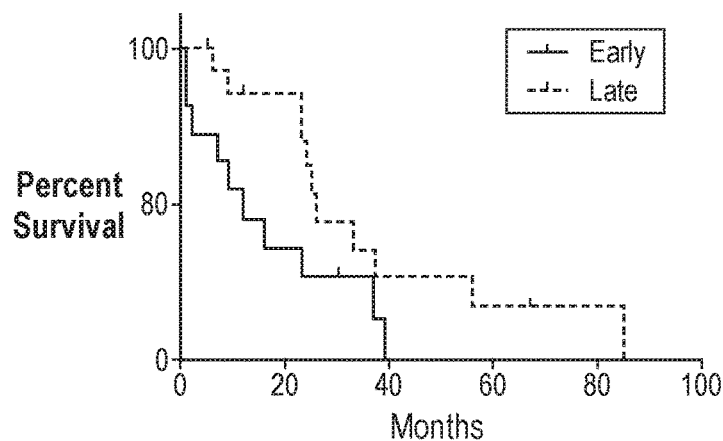
FIGS. 7A-7F are Kaplan-Meier plots for survival for patients with RAEB according to classifier label, Early or Late. The results are shown at each stage of the class label refinement process (successive iterations of loop 142 of FIG. 1). The final classifier result is shown in panel FIG. 7E and the last panel FIG. 7F compares the results for this classifier with the stratification obtained from the classifications for the RAEB samples from the classifier trained on all MDS samples (performance results shown in FIG. 3).
Figure 7B:
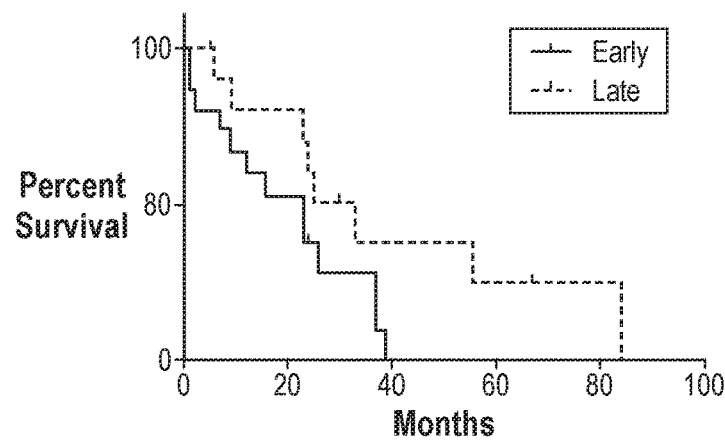
Figure 7C:
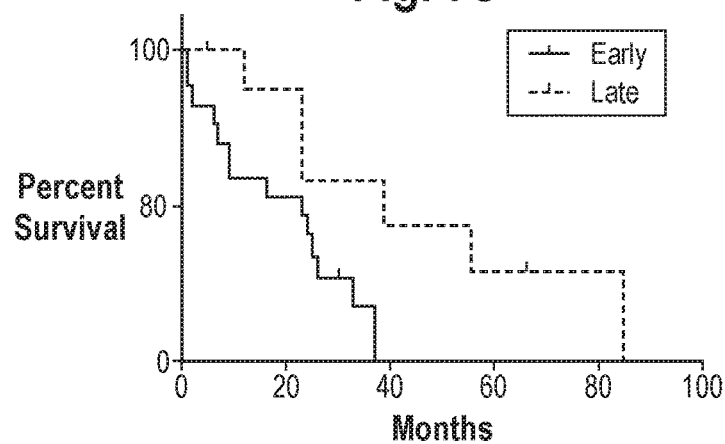
Figure 7D:
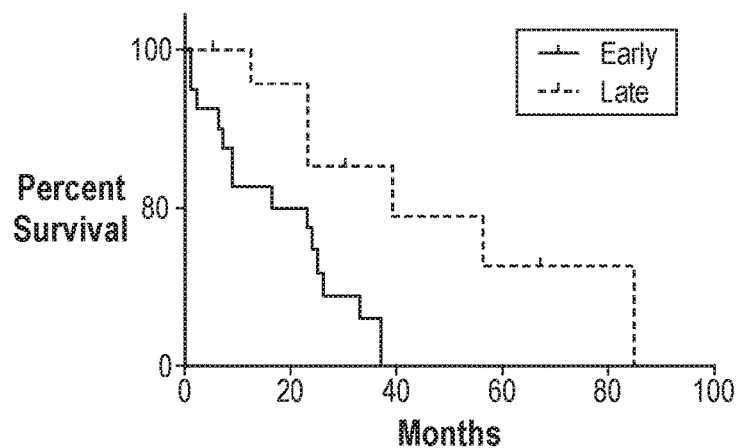
Figure 7E:
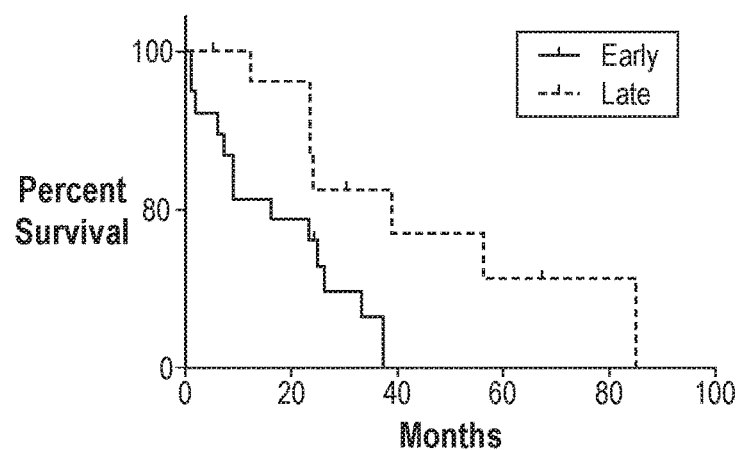
Figure 7F:
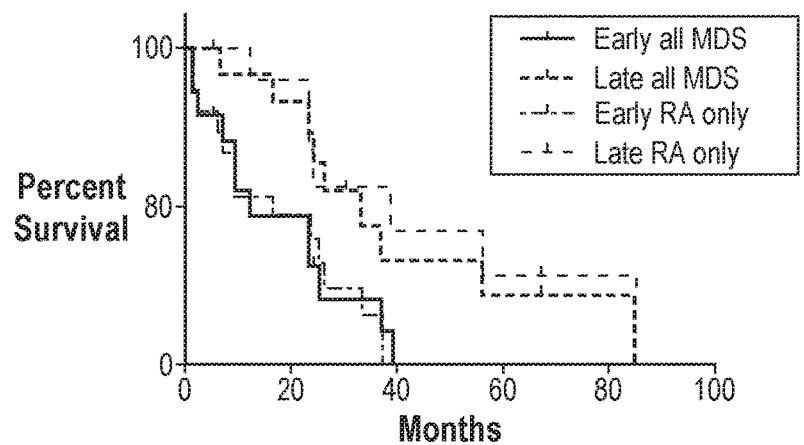

FIGS. 7A-7F are Kaplan-Meier plots for survival for patients with RAEB according to classifier label, Early or Late. The results are shown at each stage of the class label refinement process (successive iterations of loop 142 of FIG. 1). The final classifier result is shown in panel of FIG. 7E and the last panel FIG. 7F compares the results for this classifier with the stratification obtained from the classifications for the RAEB samples from the classifier trained on all MDS samples (shown in FIG. 3).

For the final RAEB classifier (FIG. 7E) the hazard ratio between Early and Late groups is 0.35 (95% CI: 0.12-0.66), log-rank p value 0.009. The median survival is 16 months (95% CI: 2-26 months) in the Early group compared with 39 months (95% CI: 12-85 months) in the Late group. The classifications assigned to each RAEB sample by this classifier are listed in Appendix D of our prior provisional application. The panel 7F compares the classifications obtained for the RAEB samples between this classifier and the classifier trained on the set of all MDS samples (FIG. 3). Similarly to the RA case, the RAEB-trained classifier assigns slightly fewer patients to the good prognosis group. However, in this case there is little difference in practical performance.

Conclusions

Classifiers were constructed with the ability to stratify MDS patients into those with better or worse survival. The classifiers perform well, as indicated in the Kaplan-Meier plots of FIGS. 3, 4, 5, 6 and 7. The groupings demonstrated a large effect size between groups in Kaplan-Meier analysis of survival. Most importantly, while the classifications generated were correlated with other prognostic factors, such as IPSS score and genetic category, multivariate and subgroup analysis showed that they had significant independent prognostic power complementary to the existing prognostic factors. In particular, the classifications obtained showed clear power to stratify patients typically defined as low risk under existing criteria and, within the refractory anemia population, it was able to identify a group of patients who experienced no deaths within 30 months of follow up. While these results have not yet been validated on an independent sample set, the classifiers of this disclosure appear to be of clinical relevance as an extra factor in assessing prognosis for MDS patients and guiding treatment of such patients.

II. Laboratory Test Center and Computer Configured as Classifier

FIG. 8 is an illustration of a laboratory testing center or system for processing a test sample (in this example a blood-based sample from an MDS patient) using a classifier generated in accordance with FIG. 1 and generating a prognostic label for the patient. The system includes a mass spectrometer 806 and a general purpose computer 810 having CPU 812 implementing a CMC/D classifier 820 coded as machine-readable instructions and a reference mass spectral data set including a feature table 822 of class-labeled mass spectrometry data stored in memory 814. It will be appreciated that the mass spectrometer 806 and computer 810 of FIG. 8 could be used to generate the CMC/D classifier 820 in accordance with the process of FIG. 1.

The operation of the system of FIG. 8 will be described in the context of a predictive test for prognosis of an MDS patient. The following discussion assumes that the CMC/D classifier 820 is already generated at the time of use of the classifier to generate a label or panel of labels for a test sample.

The system of FIG. 8 obtains a multitude of samples 800, e.g., blood-based samples (serum or plasma) from diverse MDS patients and generates a label or panel of labels as a fee-for-service. The samples 800 are used by the classifier (implemented in the computer 810) to make predictions as to the prognosis of a MDS patient. The outcome of the test is a binary class label (or panel of such labels), such as Low Risk, Late or the like, or High Risk, Early, or the like. The particular moniker for the class label is not particularly important and could be generic such as "class 1", "class 2" or the like, but as noted earlier the class label is associated with a clinical attribute relevant to the question being answered by the classifier, in this case, prognosis.

The samples may be obtained on serum cards or the like in which the blood-based sample is blotted onto a cellulose or other type card. Aliquots of the sample are spotted onto several spots of a MALDI-ToF sample "plate" 802 and the plate inserted into a MALDI-ToF mass spectrometer 806. The mass spectrometer 806 acquires mass spectra 808 from each of the spots of the sample. The mass spectra are represented in digital form and supplied to a programmed general purpose computer 810. The computer 810 includes a central processing unit 812 executing programmed instructions. The memory 814 stores the data representing the mass spectra 808. The spectral acquisition details, including deep-MALDI (100,000+laser shots) and spectra processing that was used in classifier generation (described at length above) is also used for a test sample.

The memory 814 also stores a final CMC/D classifier 820, which includes a) a reference mass spectral data set 822 in the form of a feature table of N class-labeled spectra, where N is some integer number, in this example the development set used to develop the classifier as explained above or some sub-set of the development sample set. The final CMC/D classifier includes b) code 824 representing a KNN classification algorithm (which is implemented in the mini-classifiers as explained above), c) program code 826 for executing the final classifier generated in accordance with FIG. 1 on the mass spectra of patients, including logistic regression weights and data representing master classifier(s) forming the final classifier, and d) a data structure 828 for storing classification results, including a final class label for the test sample. The memory 814 also stores program code 830 for implementing the processing shown at 850, including code (not shown) for acquiring the mass spectral data from the mass spectrometer in step 852; a pre-processing routine 832 for implementing the background subtraction, normalization and alignment step 854 (details explained above), filtering and averaging of the 800 shot spectra at multiple locations per spot and over multiple MALDI spots to make a single 100,000+shot average spectrum (as explained above), a module (not shown) for calculating integrated intensity values at predefined m/z positions in the background subtracted, normalized and aligned spectrum (step 856), and a code routine 838 for implementing the final classifier 820 using the reference dataset 822 on the values obtained at step 856. The process 858 produces a class label at step 860. The module 840 reports the class label as indicated at 860 (i.e., "Early", "Late" or the equivalent). As explained previously, the classifier 820 may be replicated so as to constitute different classifiers, e.g., to generate a panel of classification results, each one using the same feature table 822, and KNN classification algorithm 824.

The program code 830 can include additional and optional modules, for example a feature correction function code 836 (described in co-pending U.S. patent application Ser. No. 14/486,442) for correcting fluctuations in performance of the mass spectrometer, a set of routines for processing the spectrum from a reference sample to define a feature correction function, a module storing feature dependent noise characteristics and generating noisy feature value realizations and classifying such noisy feature value realizations, modules storing statistical algorithms for obtaining statistical data on the performance of the classifier on the noisy feature value realizations, or modules to combine class labels defined from multiple individual replicate testing of a sample to produce a single class label for that sample. Still other optional software modules could be included as will be apparent to persons skilled in the art.

The system of FIG. 8 can be implemented as a laboratory test processing center obtaining a multitude of patient samples from oncologists, patients, clinics, etc., and generating a class label for the patient samples as a fee-for-service. The mass spectrometer 806 need not be physically located at the laboratory test center but rather the computer 810 could obtain the data representing the mass spectra of the test sample over a computer network.

Further Considerations

It will be noted that the classifier we generated uses the features of Appendix A (or some subset, such as 100 features selected by t-statistic) and we have not determined precisely what proteins these peaks correspond to. Nor is it necessary. What matters is classifier performance. We believe that they may involve, directly or indirectly, one or more of the protein biomarkers mentioned in the scientific literature cited at the beginning of this document. Note that, with our "deep MALDI" mass spectrometry and the use of 50, 100 or even 300 or more peaks, it is likely that our classifiers are based on still undiscovered protein biomarkers circulating in serum. Our method essentially takes advantage of the fact that we can detect these proteins, and in particular low abundance proteins, using the >100,000 shot MALDI-TOF mass spectra, and use them in development of a classifier, even though we do not know precisely what proteins the peaks correspond to.

The following claims are offered as further description of the disclosed inventions.

| Appendix A: Feature definitions | | |
| --- | --- | --- |
| Left m/z | Center | Right m/z |
| 3033 | 3043 | 3054 |
| 3076 | 3086 | 3097 |
| 3099 | 3109 | 3119 |
| 3120 | 3130 | 3140 |
| 3148 | 3155 | 3162 |
| 3157 | 3168 | 3178 |
| 3176 | 3186 | 3197 |
| 3192 | 3201 | 3209 |
| 3210 | 3220 | 3230 |
| 3231 | 3241 | 3252 |
| 3255 | 3264 | 3274 |
| 3275 | 3287 | 3299 |
| 3300 | 3320 | 3339 |
| 3357 | 3369 | 3382 |
| 3382 | 3395 | 3409 |
| 3410 | 3423 | 3436 |
| 3437 | 3447 | 3457 |
| 3457 | 3467 | 3477 |
| 3478 | 3487 | 3497 |
| 3497 | 3511 | 3525 |
| 3541 | 3555 | 3570 |
| 3570 | 3578 | 3586 |
| 3586 | 3596 | 3605 |
| 3606 | 3627 | 3649 |
| 3649 | 3658 | 3667 |
| 3668 | 3682 | 3696 |
| 3696 | 3706 | 3716 |
| 3716 | 3726 | 3737 |
| 3746 | 3754 | 3762 |
| 3764 | 3775 | 3787 |
| 3788 | 3796 | 3804 |
| 3805 | 3819 | 3833 |
| 3833 | 3843 | 3852 |
| 3885 | 3892 | 3899 |
| 3900 | 3908 | 3916 |
| 3916 | 3922 | 3929 |
| 3929 | 3936 | 3943 |
| 3943 | 3952 | 3962 |
| 3962 | 3971 | 3981 |
| 4000 | 4014 | 4028 |
| 4028 | 4035 | 4042 |
| 4042 | 4051 | 4060 |
| 4060 | 4069 | 4078 |
| 4103 | 4110 | 4116 |
| 4116 | 4121 | 4126 |
| 4276 | 4289 | 4301 |
| 4304 | 4315 | 4326 |
| 4329 | 4339 | 4350 |
| 4350 | 4360 | 4370 |
| 4371 | 4379 | 4387 |
| 4381 | 4391 | 4401 |

Appendix A: Feature definitions

| Left m/z | Center | Right m/z |
| --- | --- | --- |
| 4396 | 4410 | 4425 |
| 4426 | 4437 | 4448 |
| 4449 | 4458 | 4466 |
| 4462 | 4472 | 4482 |
| 4485 | 4493 | 4500 |
| 4509 | 4520 | 4531 |
| 4540 | 4548 | 4557 |
| 4557 | 4568 | 4579 |
| 4579 | 4586 | 4592 |
| 4592 | 4600 | 4609 |
| 4616 | 4625 | 4633 |
| 4634 | 4644 | 4653 |
| 4648 | 4655 | 4662 |
| 4659 | 4666 | 4673 |
| 4699 | 4709 | 4720 |
| 4720 | 4731 | 4743 |
| 4747 | 4756 | 4764 |
| 4766 | 4774 | 4782 |
| 4783 | 4791 | 4799 |
| 4799 | 4809 | 4819 |
| 4819 | 4825 | 4831 |
| 4848 | 4856 | 4864 |
| 4865 | 4871 | 4878 |
| 4880 | 4892 | 4905 |
| 4906 | 4917 | 4927 |
| 4928 | 4938 | 4948 |
| 4949 | 4961 | 4974 |
| 5008 | 5018 | 5028 |
| 5028 | 5034 | 5041 |
| 5050 | 5066 | 5081 |
| 5067 | 5081 | 5095 |
| 5087 | 5104 | 5121 |
| 5122 | 5136 | 5150 |
| 5150 | 5158 | 5165 |
| 5166 | 5184 | 5203 |
| 5203 | 5212 | 5221 |
| 5215 | 5231 | 5247 |
| 5240 | 5248 | 5256 |
| 5275 | 5289 | 5303 |
| 5312 | 5325 | 5337 |
| 5353 | 5362 | 5371 |
| 5371 | 5382 | 5393 |
| 5386 | 5392 | 5398 |
| 5397 | 5408 | 5418 |
| 5421 | 5430 | 5439 |
| 5439 | 5449 | 5460 |
| 5467 | 5475 | 5483 |
| 5484 | 5492 | 5500 |
| 5501 | 5507 | 5513 |
| 5513 | 5523 | 5532 |
| 5541 | 5554 | 5567 |
| 5575 | 5587 | 5598 |
| 5625 | 5638 | 5651 |
| 5665 | 5676 | 5688 |
| 5688 | 5698 | 5708 |
| 5698 | 5709 | 5720 |
| 5711 | 5719 | 5727 |
| 5749 | 5768 | 5787 |
| 5802 | 5816 | 5830 |
| 5831 | 5855 | 5880 |
| 5881 | 5894 | 5906 |
| 5897 | 5929 | 5961 |
| 5924 | 5935 | 5945 |
| 5978 | 5988 | 5998 |
| 5998 | 6007 | 6017 |
| 6018 | 6030 | 6041 |
| 6050 | 6064 | 6079 |
| 6079 | 6088 | 6096 |
| 6096 | 6107 | 6118 |
| 6118 | 6126 | 6135 |
| 6135 | 6150 | 6166 |
| 6180 | 6194 | 6207 |
| 6207 | 6220 | 6232 |
| 6277 | 6294 | 6310 |
| 6322 | 6331 | 6340 |
| 6340 | 6352 | 6363 |
| 6357 | 6368 | 6379 |
| 6377 | 6386 | 6394 |
| 6394 | 6401 | 6409 |
| 6418 | 6433 | 6448 |
| 6448 | 6456 | 6465 |
| 6465 | 6475 | 6485 |
| 6487 | 6496 | 6505 |
| 6504 | 6512 | 6520 |
| 6512 | 6527 | 6542 |
| 6602 | 6624 | 6646 |
| 6647 | 6656 | 6664 |
| 6665 | 6675 | 6685 |
| 6686 | 6697 | 6708 |
| 6709 | 6729 | 6748 |
| 6786 | 6799 | 6811 |
| 6812 | 6830 | 6848 |
| 6824 | 6836 | 6848 |
| 6849 | 6859 | 6869 |
| 6869 | 6887 | 6905 |
| 6910 | 6919 | 6927 |
| 6928 | 6943 | 6958 |
| 6958 | 6968 | 6978 |
| 6978 | 6988 | 6998 |
| 7024 | 7049 | 7075 |
| 7117 | 7138 | 7160 |
| 7176 | 7185 | 7194 |
| 7190 | 7205 | 7220 |
| 7235 | 7247 | 7258 |
| 7254 | 7265 | 7276 |
| 7288 | 7297 | 7307 |
| 7344 | 7355 | 7366 |
| 7368 | 7386 | 7404 |
| 7454 | 7469 | 7485 |
| 7475 | 7486 | 7497 |
| 7493 | 7505 | 7518 |
| 7547 | 7565 | 7584 |
| 7599 | 7615 | 7631 |
| 7633 | 7645 | 7656 |
| 7657 | 7673 | 7689 |
| 7722 | 7737 | 7753 |
| 7753 | 7776 | 7799 |
| 7799 | 7821 | 7843 |
| 7917 | 7936 | 7955 |
| 7982 | 7995 | 8008 |
| 8021 | 8043 | 8066 |
| 8068 | 8082 | 8096 |
| 8117 | 8141 | 8164 |
| 8186 | 8203 | 8220 |
| 8222 | 8237 | 8252 |
| 8337 | 8357 | 8378 |
| 8399 | 8420 | 8440 |
| 8459 | 8476 | 8492 |
| 8515 | 8528 | 8541 |
| 8547 | 8573 | 8599 |
| 8613 | 8633 | 8653 |
| 8582 | 8651 | 8720 |
| 8649 | 8657 | 8665 |
| 8665 | 8683 | 8702 |
| 8750 | 8764 | 8778 |
| 8793 | 8809 | 8825 |
| 8855 | 8868 | 8880 |
| 8895 | 8911 | 8927 |
| 8922 | 8932 | 8941 |
| 8944 | 8958 | 8971 |
| 9002 | 9017 | 9032 |
| 9062 | 9074 | 9086 |
| 9101 | 9128 | 9155 |
| 9140 | 9167 | 9194 |
| 9276 | 9302 | 9328 |
| 9322 | 9338 | 9353 |
| 9345 | 9357 | 9370 |
| 9391 | 9441 | 9491 |
| 9554 | 9573 | 9592 |
| 9607 | 9633 | 9660 |

Appendix A: Feature definitions

| Left m/z | Center | Right m/z |
|---|---|---|
| 9687 | 9707 | 9726 |
| 9727 | 9745 | 9763 |
| 9764 | 9783 | 9802 |
| 9897 | 9923 | 9949 |
| 9931 | 9963 | 9994 |
| 10051 | 10069 | 10088 |
| 10089 | 10104 | 10120 |
| 10157 | 10189 | 10221 |
| 10243 | 10272 | 10301 |
| 10323 | 10337 | 10351 |
| 10368 | 10389 | 10409 |
| 10426 | 10443 | 10460 |
| 10462 | 10488 | 10514 |
| 10516 | 10531 | 10547 |
| 10562 | 10579 | 10596 |
| 10601 | 10649 | 10696 |
| 10699 | 10727 | 10755 |
| 10814 | 10840 | 10865 |
| 10913 | 10935 | 10957 |
| 10983 | 11004 | 11026 |
| 11026 | 11046 | 11065 |
| 11072 | 11098 | 11125 |
| 11126 | 11145 | 11164 |
| 11268 | 11298 | 11328 |
| 11339 | 11365 | 11390 |
| 11391 | 11403 | 11416 |
| 11417 | 11436 | 11455 |
| 11455 | 11470 | 11485 |
| 11498 | 11526 | 11554 |
| 11607 | 11623 | 11640 |
| 11651 | 11680 | 11708 |
| 11714 | 11728 | 11743 |
| 11765 | 11780 | 11794 |
| 11852 | 11888 | 11923 |
| 11924 | 11943 | 11963 |
| 11975 | 12018 | 12062 |
| 12144 | 12167 | 12190 |
| 12247 | 12283 | 12319 |
| 12365 | 12382 | 12399 |
| 12420 | 12450 | 12480 |
| 12531 | 12561 | 12591 |
| 12591 | 12611 | 12631 |
| 12644 | 12661 | 12678 |
| 12679 | 12689 | 12700 |
| 12712 | 12730 | 12749 |
| 12818 | 12856 | 12895 |
| 12940 | 12957 | 12974 |
| 12964 | 12980 | 12995 |
| 13041 | 13075 | 13109 |
| 13111 | 13128 | 13144 |
| 13144 | 13162 | 13180 |
| 13224 | 13239 | 13254 |
| 13262 | 13274 | 13287 |
| 13299 | 13315 | 13331 |
| 13342 | 13356 | 13370 |
| 13371 | 13390 | 13410 |
| 13517 | 13544 | 13572 |
| 13588 | 13607 | 13625 |
| 13692 | 13714 | 13735 |
| 13735 | 13756 | 13777 |
| 13777 | 13794 | 13811 |
| 13821 | 13837 | 13854 |
| 13854 | 13875 | 13897 |
| 13897 | 13910 | 13923 |
| 13923 | 13939 | 13954 |
| 13955 | 13977 | 14000 |
| 14010 | 14032 | 14055 |
| 14028 | 14050 | 14071 |
| 14075 | 14089 | 14103 |
| 14127 | 14148 | 14169 |
| 14177 | 14197 | 14218 |
| 14220 | 14250 | 14281 |
| 14366 | 14403 | 14439 |
| 14458 | 14483 | 14508 |
| 14514 | 14530 | 14546 |
| 14547 | 14562 | 14577 |
| 14591 | 14623 | 14656 |
| 14746 | 14778 | 14811 |
| 14848 | 14878 | 14908 |
| 14948 | 14969 | 14991 |
| 15271 | 15292 | 15313 |
| 15314 | 15347 | 15380 |
| 15518 | 15557 | 15596 |
| 15598 | 15630 | 15663 |
| 15972 | 15989 | 16005 |
| 16018 | 16032 | 16047 |
| 16057 | 16084 | 16111 |
| 16150 | 16175 | 16199 |
| 16442 | 16498 | 16555 |
| 16588 | 16661 | 16734 |
| 17004 | 17025 | 17046 |
| 17034 | 17058 | 17081 |
| 17107 | 17123 | 17140 |
| 17140 | 17166 | 17191 |
| 17212 | 17273 | 17334 |
| 17337 | 17391 | 17444 |
| 17445 | 17459 | 17474 |
| 17474 | 17504 | 17535 |
| 17544 | 17576 | 17608 |
| 17600 | 17638 | 17676 |
| 17799 | 17889 | 17979 |
| 17981 | 18011 | 18041 |
| 18042 | 18072 | 18102 |
| 18103 | 18151 | 18200 |
| 18228 | 18270 | 18311 |
| 18584 | 18621 | 18658 |
| 18659 | 18704 | 18749 |
| 18754 | 18783 | 18813 |
| 18813 | 18841 | 18869 |
| 18870 | 18899 | 18928 |
| 19337 | 19484 | 19631 |
| 19888 | 19935 | 19983 |
| 20868 | 20935 | 21002 |
| 21003 | 21064 | 21125 |
| 21126 | 21176 | 21226 |
| 21226 | 21281 | 21337 |
| 21659 | 21699 | 21739 |

We claim:

1. A method of detecting a class label in a myelodysplastic syndrome (MDS) patient comprising the steps of:
  (a) performing MALDI-TOF mass spectrometry on a blood-based sample obtained from the MDS patient by subjecting the sample to at least 100,000 laser shots and acquiring mass spectral data;
  (b) obtaining integrated intensity values in the mass spectral data of a multitude of pre-determined mass-spectral features, wherein the mass-spectral features include a multitude of features listed in Appendix A, wherein the obtaining step (b) comprises obtaining integrated intensity values of at least 50 features listed in Appendix A; and
  (c) operating on the integrated intensity values of the mass spectral data with a programmed computer implementing a classifier;
  wherein in the operating step the classifier compares the integrated intensity values with feature values of a training set of class-labeled mass spectral data obtained from a multitude of other MDS patients with the values obtained in step (b) with a classification algorithm and detects a class label for the sample, wherein when the class label for the sample indicates that the MDS patient has a relatively poor prognosis, administering hematopoietic stem cell transplants (HSCTs), high intensity chemotherapy, supportive care or combinations thereof to the MDS patient.

2. The method of claim 1, wherein the classifier is configured as a combination of filtered mini-classifiers using a regularized combination method.

3. The method of claim 1, wherein the obtaining step (b) comprises obtaining integrated intensity values of at least 100 features listed in Appendix A.

4. The method of claim 1, wherein the obtaining step (b) comprises obtaining integrated intensity values of at least 300 features listed in Appendix A.

5. The method of claim 1, wherein the high intensity chemotherapy is azacitidine or decitabine.

6. A method of detecting a class label in a myelodysplastic syndrome (MDS) patient comprising the steps of:
   (a) performing MALDI-TOF mass spectrometry on a blood-based sample obtained from the MDS patient by subjecting the sample to at least 100,000 laser shots and acquiring mass spectral data;
   (b) obtaining integrated intensity values in the mass spectral data of a multitude of pre-determined mass-spectral features, wherein the mass-spectral features include a multitude of features listed in Appendix A, wherein the obtaining step (b) comprises obtaining integrated intensity values of at least 50 features listed in Appendix A; and
   (c) operating on the integrated intensity values of the mass spectral data with a programmed computer implementing a classifier;
   wherein in the operating step the classifier compares the integrated intensity values with feature values of a training set of class-labeled mass spectral data obtained from a multitude of other MDS patients with the values obtained in step (b) with a classification algorithm and detects a class label for the sample, wherein when the class label for the sample indicates that the MDS patient has a relatively good prognosis, administering lenalidomide, immunosuppressive therapy, azacytidine, or supportive therapy to the MDS patient.

7. The method of claim 6, wherein the classifier is configured as a combination of filtered mini-classifiers using a regularized combination method.

8. The method of claim 6, wherein the obtaining step (b) comprises obtaining integrated intensity values of at least 100 features listed in Appendix A.

9. The method of claim 6, wherein the obtaining step (b) comprises obtaining integrated intensity values of at least 300 features listed in Appendix A.

10. A method of guiding treatment of a myelodysplastic syndrome (MDS) patient comprising the steps of:
    (a) performing MALDI-TOF mass spectrometry on a blood-based sample obtained from the MDS patient by subjecting the sample to at least 100,000 laser shots and acquiring mass spectral data;
    (b) performing a classification of the mass spectral data with the aid of a computer implementing a classifier, wherein the classifier is developed from a development set of samples from other MDS patients comprising iteratively training a classifier from the development set of samples and a multitude of mass spectral features listed in Appendix A to generate a class label; and
    (c) supplying the mass spectrometry data of the sample obtained in step a) to the classifier implemented in a programmed computer trained to predict whether a melanoma patient is in a high risk group, wherein when the patient is classified into the high risk group the patient is predicted to be likely to benefit from hematopoietic stem cell transplants (HSCTs), high intensity chemotherapy, azacytidine, decitabine, supportive care, or combinations thereof.

11. The method of claim 10, wherein where the patient is classified into the high risk group the patient administered hematopoietic stem cell transplants (HSCTs), high intensity chemotherapy, azacytidine, decitabine, supportive care, or combinations thereof.

\* \* \* \* \*